(12) United States Patent
Zhang et al.

(10) Patent No.: US 8,133,918 B2
(45) Date of Patent: *Mar. 13, 2012

(54) AQUEOUS PHARMACEUTICAL COMPOSITIONS OF 2,6-DIISOPROPYLPHENOL (PROPOFOL) AND THEIR USES

(75) Inventors: Zhong Zhang, Sudbury, MA (US); Orn Almarsson, Shrewsbury, MA (US); Hongming Chen, Acton, MA (US)

(73) Assignee: Janssen Biotech, Inc., Horsham, PA (US)

( * ) Notice: Subject to any disclaimer, the term of this patent is extended or adjusted under 35 U.S.C. 154(b) by 289 days.

This patent is subject to a terminal disclaimer.

(21) Appl. No.: 12/333,887

(22) Filed: Dec. 12, 2008

(65) Prior Publication Data

US 2009/0093549 A1    Apr. 9, 2009

Related U.S. Application Data

(63) Continuation of application No. 10/766,631, filed on Jan. 28, 2004, now Pat. No. 7,550,155, which is a continuation-in-part of application No. 10/629,308, filed on Jul. 29, 2003, and a continuation-in-part of application No. 10/677,747, filed on Oct. 2, 2003, now abandoned.

(60) Provisional application No. 60/485,354, filed on Jul. 7, 2003, provisional application No. 60/470,403, filed on May 14, 2003, provisional application No. 60/464,314, filed on Apr. 21, 2003, provisional application No. 60/462,450, filed on Apr. 11, 2003, provisional application No. 60/443,490, filed on Jan. 29, 2003, provisional application No. 60/436,979, filed on Dec. 30, 2002, provisional application No. 60/422,195, filed on Oct. 29, 2002, provisional application No. 60/399,490, filed on Jul. 29, 2002.

(30) Foreign Application Priority Data

Jul. 29, 2003 (WO) ............... PCT/US03/23512
Oct. 2, 2003 (WO) ............... PCT/US03/31086

(51) Int. Cl.
   *A61K 31/05* (2006.01)
   *A61K 31/14* (2006.01)
(52) U.S. Cl. ................... 514/731; 514/643
(58) Field of Classification Search .......... 514/731, 514/643
See application file for complete search history.

(56) References Cited

U.S. PATENT DOCUMENTS

| | | | |
|---|---|---|---|
| 4,056,635 A | 11/1977 | Glen et al. | |
| 4,452,817 A | 6/1984 | Glen et al. | |
| 4,798,846 A | 1/1989 | Glen et al. | |
| 5,296,161 A | 3/1994 | Wiersema et al. | |
| 5,635,540 A | 6/1997 | Edlich et al. | |
| 5,637,625 A | 6/1997 | Haynes | |
| 5,731,355 A | 3/1998 | Jones et al. | |
| 5,962,536 A | 10/1999 | Komer | |
| 6,077,545 A * | 6/2000 | Roskos et al. | 424/649 |
| 6,100,302 A | 8/2000 | Pejaver et al. | |
| 6,140,373 A | 10/2000 | May et al. | |
| 6,140,374 A | 10/2000 | May et al. | |
| 6,150,423 A | 11/2000 | Carpenter | |
| 6,277,410 B1 | 8/2001 | Kabanov et al. | |
| 6,383,471 B1 | 5/2002 | Chen et al. | |
| 6,534,547 B1 | 3/2003 | Carpenter | |
| 6,623,765 B1 | 9/2003 | Dennis et al. | |
| 6,638,537 B2 | 10/2003 | Dennis et al. | |
| 6,743,436 B1 | 6/2004 | Lee et al. | |
| 7,034,013 B2 | 4/2006 | Thompson et al. | |
| 7,166,303 B2 | 1/2007 | Meadows et al. | |
| 2002/0006442 A1 | 1/2002 | Mishra et al. | |
| 2002/0022667 A1 | 2/2002 | Pace et al. | |
| 2002/0107291 A1 | 8/2002 | Tommaso | |
| 2003/0138489 A1 | 7/2003 | Meadows et al. | |
| 2003/0165544 A1 | 9/2003 | Mishra et al. | |
| 2004/0220283 A1 | 11/2004 | Zhang et al. | |
| 2004/0265388 A1 | 12/2004 | Zhang et al. | |
| 2005/0009731 A1 | 1/2005 | Desai et al. | |
| 2005/0027019 A1 | 2/2005 | Zhang et al. | |

FOREIGN PATENT DOCUMENTS

| | | |
|---|---|---|
| GB | 2 298 789 A | 9/1996 |
| JP | 2002-521434 | 7/2002 |
| WO | WO 97/10814 | 3/1997 |
| WO | WO 00/06142 A1 | 2/2000 |
| WO | WO 00/21517 | 4/2000 |
| WO | WO 00/24376 A1 | 5/2000 |
| WO | WO 00/78301 | 12/2000 |
| WO | WO 01/64187 | 9/2001 |

(Continued)

OTHER PUBLICATIONS

Japan Pharmaceutical Excipients Council edit, Pharmaceutical Excipients Directory, section "propylene glycol," 1994, pp. 114.

(Continued)

*Primary Examiner* — Brandon Fetterolf
*Assistant Examiner* — Shirley V Gembeh
(74) *Attorney, Agent, or Firm* — RatnerPrestia

(57) ABSTRACT

The present invention provides aqueous pharmaceutical compositions containing a lipophilic therapeutic agent. In particular, the invention provides aqueous pharmaceutical compositions containing the compound 2,6-diisopropylphenol (propofol). Preferred compositions of the invention contain propofol in the presence of at least one block copolymer (for example, P188 or another poloxamer) and a polyethylene glycol (PEG). Compositions of the invention are preferably sterile or are readily sterilized (e.g., by autoclaving) and are suitable for parenteral administration to any animal, including humans. The compositions are also chemically and physically stable over a wide range of environmental conditions and for extended periods of time.

29 Claims, 7 Drawing Sheets

FOREIGN PATENT DOCUMENTS

| WO | WO 01/89514 | 11/2001 |
|---|---|---|
| WO | WO 01/97779 A2 | 12/2001 |
| WO | WO 01/97796 A1 | 12/2001 |
| WO | WO 02/09671 A1 | 2/2002 |
| WO | WO 02/45709 A1 | 6/2002 |
| WO | WO 02/074200 A1 | 9/2002 |
| WO | WO 03/017977 | 3/2003 |
| WO | WO 03/030862 | 4/2003 |
| WO | WO 2004/032910 A | 4/2004 |

OTHER PUBLICATIONS

Non-Final Office Action of U.S. Appl. No. 10/629,308, dated Jul. 7, 2009.
Amendment in response to Non-Final Office Action of U.S. Appl. No. 10/629,308, filed Oct. 7, 2009.
M. L. Adams, et al., "Amphiphilic Block Copolymers for Drug Delivery" Journal of Pharmaceutical Sciences, vol. 92, No. 7, Jul. 2003.
S. Dutta, et al., "Formulation-dependent Pharmacokinetics and Pharmacodynamics of Propofol in Rats", J. Pharm. Pharmacol., 1998, 50: 37-42.
R. Invanova, et al., "Interaction of Poloxamer Block Copolymers with Cosolvents and Surfactants", Colloids and Surfaces, Physiochemical and Engineering Aspects 183-185 (2001) p. 41-53.
K. Momot, et al. "NMR Study of the Association of Propofol with Nonionic Surfactants", Langmuir 2003, 19, p. 2088-2095.
P. Bulet et al., "Antimicrobial Peptides in Insects; Structure and Function", Developmental and Comparative Immunology, 23 (1999), pp. 329-344.
R. Challa et al., "Cyclodextrins in Drug Delivery: An Updated Review", AAPS PharmaSciTech 2005; Oct. 14, 2005, pp. E329-E357, 6 (2) Article 43, Department of Pharmaceutics, Faculty of Pharmacy, Hamdard University, New Delhi India.
T. Lofisson et al., "Cyclodextrins in Drug Delivery", Expert Opinion Drug Delivery, 2005, 2 (2), p. 335-351, Ashley Publications, University of Iceland, Faculty of Pharmacy, Hagi, Hofivallagata, Iceland.
Official Action of Jul. 28, 2005 in U.S. Appl. No. 10/629,308.
Amendment filed Dec. 23, 2005 in response to Official Action of Jul. 28, 2005 in U.S. Appl. No. 10/629,308.
Official Action of Feb. 27, 2006 in U.S. Appl. No. 10/629,308.
Official Action of Jun. 29, 2006 in U.S. Appl. No. 10/629,308.
Amendment filed Aug. 18, 2006 in response to Official Action of Jun. 29, 2006 in U.S. Appl. No. 10/629,308.
Advisory Action of Dec. 22, 2006 in U.S. Appl. No. 10/629,308.
Amendment filed Nov. 19, 2008 in U.S. Appl. No. 10/629,308.
Amendment filed Mar. 2, 2007 in response to Official Action of Dec. 22, 2006 in U.S. Appl. No. 10/629,308.
Official Action of Nov. 5, 2007 in U.S. Appl. No. 10/629,308.
Official Action of Jul. 28, 2005 in U.S. Appl. No, 10/677,747.
Amendment filed Nov. 28, 2005 to Official Action of Jul. 28, 2005 in U.S. Appl. No. 10/677,747.
Official Action of Feb. 27, 2006 in U.S. Appl. No. 10/677,747.
Official Action of Jun. 30, 2006 in U.S. Appl. No. 10/677,747.
Amendment filed Sep. 1, 2006 in response to Official Action of Jun. 30, 2006 in U.S. Appl. No. 10/677,747.
Official Action of Dec. 22, 2006 in U.S. Appl. No. 10/677,747.
Amendment filed Feb. 6, 2007 in response to Official Action of Dec. 22, 2006 in U.S. Appl. No. 10/677,747.
Official Action of Jul. 5, 2007 in U.S. Appl. No. 10/677,747.
Amendment filed Oct. 4, 2007 in response to Official Action of Jul. 5, 2007 in U.S. Appl. No. 10/677,747.
Amendment filed May 2, 2008 in response to Official Action of Nov. 5, 2007 in U.S. Appl. No. 10/629,308.
Official Action of May 28, 2008 in U.S. Appl. No. 10/677,747.
Official Action of Aug. 19, 2008 in U.S. Appl. No. 10/629,308.
Advisory Action dated Feb. 2, 2009 in U.S. Appl. No. 10/629,308.
International Search Report of PCT/US03/31086 dated Oct. 2, 2003.

* cited by examiner

Formula (I)

Formula (II)

Formula (III)

Formual (IV)

Formula (V)

Formula (VI)

Formula (VII)

AQUEOUS PHARMACEUTICAL COMPOSITIONS OF 2,6-DIISOPROPYLPHENOL (PROPOFOL) AND THEIR USES

1. CROSS-REFERENCE TO RELATED APPLICATIONS

This application is a continuation of U.S. patent application Ser. No. 10/766,631, filed Jan. 28, 2004 now U.S. Pat. No. 7,550,155, which is a continuation-in-part of U.S. patent application Ser. Nos. 10/629,308, filed Jul. 29, 2003 and 10/677,747, filed on Oct. 2, 2003 now abandoned, and claims benefit under 35 U.S.C. 119(e) to U.S. provisional Patent application Ser. No. 60/399,490, filed Jul. 29, 2002, 60/422,195, filed Oct. 29, 2002, 60/436,979, filed Dec. 30, 2002, 60/443,490, filed Jan. 29, 2003, 60/462,450, filed Apr. 11, 2003, 60/464,314, filed Apr. 21, 2003, 60/470,403, filed May 14, 2003, and 60/485,354, filed Jul. 7, 2003. The present application also claims benefit of International Applications PCT/US03/23512, filed Jul. 29, 2003 and PCT/US03/31086, filed Oct. 2, 2003. Each of these prior applications is incorporated herein by reference, and in its entirety.

2. FIELD OF THE INVENTION

The present invention relates to aqueous pharmaceutical compositions containing a lipophilic therapeutic agent. In particular, the invention provides aqueous pharmaceutical compositions containing the compound 2,6-diisopropylphenol (propofol).

3. BACKGROUND OF THE INVENTION

The compound 2,6-diisopropylphenol is a well known anesthetic agent that is commonly known as propofol. The onset of anesthesia is largely controlled by a drug's diffusion rate through the blood-brain barrier. Propofol is lipophilic, and this property helps that compound to provide rapid anesthetic action. However, the lipophilicity of propofol also renders that compound, which is a liquid at room temperature, relatively insoluble in water. As a result, propofol is commonly administered directly into the bloodstream (either by infusion or by bolus injection) as an oil-in-water emulsion. Such formulations typically contain a lipid component to solubilize the drug. Lipids, however, are good substrates for bacterial growth and can also be incompatible with preservatives that are at least somewhat water soluble such as benzyl alcohol. Further, parenteral administration of large volumes of lipid emulsions and/or the administration of lipid emulsions over prolonged periods of time may result in hyperlipidemia.

Despite these shortcomings of such oil-in-water emulsions, propofol has been a successful anesthetic and is commercially available for human administration as Diprivan® Injectable Emulsion (AstraZeneca; Diprivan® is a trademark of Imperial Chemical Industries PLC). Propofol is also marketed for veterinary use as Rapinovet™ Anesthetic Injection (Schering-Plough Animal Heath Corp.; Rapinovet™ is a trademark of Schering-Plough Veterinary Corp.) and as PropoFlo™ Anesthetic Injection (Abbott Laboratories; PropoFlo™ is a trademark of Abbott Laboratories).

Diprivan® Injectable Emulsion is a white, oil-in-water emulsion containing, in addition to 10 milligrams propofol per milliliter of emulsion, 100 mg soybean oil per mL, 22.5 mg glycerol per mL, 12 mg egg lecithin per mL, 0.005% disodium edetate, and sodium hydroxide. Diprivan® Injectable Emulsion is indicated as a single-use parenteral product. Diprivan® contains disodium edetate to retard the growth of microorganisms in the event of accidental extrinsic contamination. However, Diprivan® can still support the growth of microorganisms. As acknowledged in the product insert, there have been reports in which failure to use antiseptic techniques when handling the emulsion was associated with microbial contamination and associated medical complications. It is therefore necessary to discard tubing and unused portions of Diprivan® after 12 hours because of the potential for microbial contamination and growth. Diprivan® must also be stored in a very narrow temperature range between 4 to 22° C. (Diprivan® Injectable Emulsion Product Insert, AstraZeneca (2001)).

PropoFlo™ Anesthetic Injection is an oil-in water emulsion containing, in addition to 10 milligrams propofol per milliliter of emulsion, 100 mg soybean oil per mL, 22.5 mg glycerol per mL, 12 mg egg lecithin per mL, and sodium hydroxide. Like Diprivan®, PropoFlo™ is capable of supporting the growth of microorganisms. Failure to follow aseptic procedures may result in microbial contamination and associated medical complications. Unused portions of PropoFlo™ must therefore be disposed of within 6 hours of vial entry (PropoFlo™ Anesthetic Injection Product Insert, Abbott Laboratories (1998)).

Rapinovet™ Anesthetic Injection is a white, oil-in-water emulsion containing, in addition to 10 milligrams propofol per milliliter of emulsion, 100 mg soybean oil/mL, 22.5 mg glycerol/mL, 12 mg egg lecithin/mL, 0.25 mg sodium metabisulfite/mL, and sodium hydroxide. Like Diprivan® and PropoFlo™, Rapinovet™ is capable of supporting the growth of microorganisms. (Rapinovet™ Anesthetic Injection Product Insert, Schering-Plough Animal Health (2000)).

GB-A-1,472,793 (see also, U.S. Pat. Nos. 4,056,635; 4,452,817; and 4,798,846) describes the use of propofol as an anesthetic and discloses certain injectable formulations of that compound. These formulations use a range of non-ionic surfactant concentrations with a water miscible, non-aqueous co-solvent such as an alcohol or glycol to solubilize an effective concentration of propofol. For example, one such formulations combines propofol with propylene glycol and a polyoxyethylen-polyoxypropylene block co-polymer known as Pluronic® F68 (Pluronic is a registered tradename used by BASF Corporation, Parsippany, N.J.) in water. Pluronic® F68 is also commonly known as Poloxamer 188 or 'P188'. However, the use of propylene glycol and other water-miscible co-solvents in such formulations is associated with undesirable medical side effects such as concomitant pain on injection, superficial thrombophlebitis and intravasal haemolytic reactions.

International patent publication No. WO 01/64187 describes aqueous preparations of propofol that use poloxamer block co-polymer and are free of propylene and other non-aqueous co-solvents. However, the publication notes that the poloxamer P188 has a very limited ability to hold propofol (only 0.8% propofol in a 10% aqueous solution of P188). As a result, the formulations described in this publication must contain mixtures of P188 and another poloxamer compound such as P407. Yet only the poloxamer P188 has been approved by the U.S. Food and Drug Administration (FDA) for use in injectable formulations. Moreover, the use of poloxamers and other block copolymers at high levels can also be associated with undesirable side effects and is generally undesirable. See, for example, Blonder et al., *Life Sci.* (1999) 65:PL261-266; and Johnston et al., *J. Cardiovasc. Pharmacol.* (1999) 34:831-842.

International patent publication no. WO 00/78301 also describes aqueous formulations of propofol in P188 or P407. However, the formulations disclosed in this publication also contain an additional surfactant, such as Solutol® HS 15 (Solutol is a registered trademark used by BASF Corporation, Parsippany, N.J.) or egg lecithin, or they contain co-solvents such as ethanol and/or polyethylene glycol. As noted above, however, the use of egg lecithin can support the growth of microorganisms, whereas co-solvents such as ethanol and polyethylene glycol can also be associated with undesirable side effects. Moreover, Solutol® is also associated with undesirable side effects and has not been approved for injectable formulations by the FDA.

Still other publications describe aqueous formulations that contain microemulsions of propofol in an oil or lipid. See, for example, International Patent Publication No. WO 00/10531. See also, U.S. Pat. Nos. 6,140,374; 6,150,423; and publication no. US 2002/0120015 A1.

Hence, there is an ongoing need for formulations of propofol and, in particular, for injectable, aqueous formulations of propofol that are sterile and stable for indefinite periods under clinical conditions. At the same time, there is a need for aqueous formulations of propofol that minimize the use of surfactants, block copolymers, co-solvents and other excipients that may produce harmful or undesired side effects.

The citation and/or discussion of a reference in this section and throughout the specification is provided merely to clarify the description of the present invention and is not an admission that any such reference is "prior art" to the invention described herein.

4. SUMMARY OF THE INVENTION

The present invention relates to aqueous pharmaceutical compositions (also referred to herein as "formulations") of therapeutic agents that are lipophilic and, consequently, not traditionally amenable to formulation in a homogenous, aqueous solution. More specifically, the invention relates to aqueous formulations of 2,6-diisopropylphenol (i.e., propofol), its derivatives and analogues, and pharmaceutically acceptable salts thereof. It has been discovered that, by combining polyethylene glycol with a block co-polymer emulsifier, it is possible to dissolve or suspend higher amounts of propofol and other lipophilic compounds while, at the same time, using smaller amounts of these excipients. As a result, it is possible to prepare stable, homogeneous aqueous formulations of propofol without using traditional emulsifiers, such as oils and/or lipids. The formulations of the invention are simple to prepare, are stable and can be readily stored for extended periods under a variety of different conditions. Moreover, because these compositions avoid the use of traditional emulsifiers which are substrates for bacterial growth, the compositions can be readily sterilized and can be preserved as sterile compositions for extended periods of time.

Preferred compositions of the invention are aqueous propofol formulations that comprise propofol in an aqueous medium with at least two excipients. Preferably, the two excipients are: (1) a block co-polymer, and (2) a polyethylene glycol (PEG). The block co-polymer can be, for example, a poloxamer such poloxamer 188 (P188), poloxamer 407 (P407) or poloxamer 237 (P237). In preferred embodiments, the block co-polymer is P188. The polyethylene glycol can be a PEG having a molecular weight of 200 (PEG-200), 300 (PEG-300), 400 (PEG-400), 600 (PEG-600), 800 (PEG-800) or 1000 (PEG-1000), with PEG-400 being particularly preferred.

Formulations of the present invention are able to contain higher levels of propofol in a homogeneous suspension or solution while, at the same time, using lower levels of excipients. Hence, preferred compositions contain at least 1% (w/v) and can have as much as 5% (w/v) propofol. In particularly preferred embodiments, formulations of the invention comprise between about 1-2% (w/v) propofol with 1% (w/v) propofol being particularly preferred.

In various embodiments, the amount of block copolymer in a formulation of the invention is less than about 10% (w/v) of the formulation, with preferred amounts being between about 5 to 10% (w/v) of the formulation, and more preferably between about 6 to 8% (w/v) of the formulation. Preferred amounts of PEG in various embodiments of the invention are less than about 5% (w/v) of the formulation, and are more preferably between about 3 and 4% (w/v) of the formulation.

In other embodiments, formulations of the invention may comprise one or more additional excipients, such as tonicity modifiers, antimicrobial agents, and/or preservatives. For example, the invention provides aqueous propofol formulations that additionally comprise a tonicity modifier selected from the group consisting of lactose, dextrose, dextrose anhydrous, mannitol, sodium chloride, potassium chloride, propylene glycol and glycerol. In a preferred embodiment, the tonicity modifier is propylene glycol, preferably in an amount that is not more than 5% (w/v) of the formulation, and more preferably not more than 2% (w/v) of the formulation.

In still other embodiments, an aqueous propofol formulation of the invention can comprise a preservative, such as citric acid, preferably at a concentration between 2.5 and 15 mM, with a concentration of about 10 mM (e.g., about 2.0 mg/ml) being particularly preferred. The invention provides additional embodiments in which an aqueous propofol formulation comprises an antimicrobial agent. In certain such embodiments the antimicrobial agent can be selected from the group consisting of disodium edetate, metabisulfate, benzyl alcohol, cysteine or a salt thereof, and EDTA. In particularly preferred embodiments, the antimicrobial agent is benzyl alcohol, preferably in an amount of up to 0.5% (w/v) of the formulation.

In particular embodiments, the invention provides aqueous propofol formulations that comprise: (a) polaxmer 188 in an amount between 6 and 8% (w/v) of the formulation, (b) PEG-400 in an amount between 2 and 4% (w/v) of the formulation, (c) propylene glycol in an amount not greater than 2% (w/v) of the formulation, and (d) 2,6-diisopropylphenol (i.e., propofol) in an amount between 1 and 2% (w/v) of the formulation. In such embodiments, the formulations can also optionally comprise: (e) citric acid at a concentration between 2.5 and 15 mM (and more preferably about 10 mM or 2 mg/ml), and (e) benzyl alcohol in an amount up to 0.5% w/v (and more preferably 0.45% w/v) of the formulation.

Specific preferred embodiments of aqueous propofol formulations are also provided, including formulations as follows:

(1) P237 in an amount of about 3% (w/v) of the formulation, PEG-400 in an amount of about 6% (w/v) of the formulation, and propofol in an amount of about 1% (w/v) of the formulation;

(2) P188 in an amount of about 8% (w/v) of the formulation, PEG-400 in an amount of about 4% (w/v) of the formulation, propylene glycol in an amount of about 1% (w/v) of the formulation, and propofol in an amount of about 1% (w/v) of the formulation;

(3) P188 in an amount of about 8% (w/v) of the formulation, PEG-400 in an amount of about 3% (w/v) of the formulation, propylene glycol in an amount of about 1% (w/v) of the formulation, and propofol in an amount of about 1% (w/v) of the formulation;

(4) P188 in an amount of about 8% (w/v) of the formulation, PEG-400 in an amount of about 4% (w/v) of the formulation, propofol in an amount of about 1% (w/v) of the formulation and substantially free of propylene glycol;

(5) P188 in an amount of about 8% (w/v) of the formulation, PEG-400 in an amount of about 3% (w/v) of the formulation, propofol in an amount of about 1% (w/v) of the formulation and substantially free of propylene glycol;

(6) P188 in an amount of about 7% (w/v) of the formulation, PEG-400 in an amount of about 4% (w/v) of the formulation, propylene glycol in an amount of about 1% (w/v) of the formulation, and propofol in an amount of about 1% (w/v) of the formulation;

(7) P188 in an amount of about 7% (w/v) of the formulation, PEG-400 in an amount of about 4% (w/v) of the formulation, propofol in an amount of about 1% (w/v) of the formulation and substantially free of propylene glycol;

(8) P188 in an amount of about 7% (w/v) of the formulation, PEG-400 in an amount of about 3% (w/v) of the formulation, propylene glycol in an amount of about 1% (w/v) of the formulation, and propofol in an amount of about 1% (w/v) of the formulation;

(9) P188 in an amount of about 7% (w/v) of the formulation, PEG-400 in an amount of about 3% (w/v) of the formulation, propofol in an amount of about 1% (w/v) of the formulation, and substantially free of propylene glycol;

(10) P188 in an amount of about 6% (w/v) of the formulation, PEG-400 in an amount of about 4% (w/v) of the formulation, propylene glycol in an amount of about 1% (w/v) of the formulation, and propofol in an amount of about 1% (w/v) of the formulation;

(11) P188 in an amount of about 6% (w/v) of the formulation, PEG-400 in an amount of about 4% (w/v) of the formulation, propylene glycol in an amount of about 2% (w/v) of the formulation, and propofol in an amount of about 1% (w/v) of the formulation;

(12) P188 in an amount of about 6% (w/v) of the formulation, PEG-400 in an amount of about 6% (w/v) of the formulation, propylene glycol in an amount of about 1% (w/v) of the formulation, and propofol in an amount of about 1% (w/v) of the formulation;

(13) P188 in an amount of about 8% (w/v) of the formulation, PEG-400 in an amount of about 4% (w/v) of the formulation, propofol in an amount of about 1% (w/v) of the formulation, and substantially free of propylene glycol; and

(14) P188 in an amount of about 9% (w/v) of the formulation, PEG-400 in an amount of about 2% (w/v) of the formulation, propofol in an amount of about 1% (w/v) of the formulation, and substantially free of propylene glycol.

In various other embodiments provided herein, any of the above-described formulations can additionally comprise citric acid, preferably at a concentration of between 2.5 and 15 mM and more preferably in an amount of about 20 mg per 10 milliliters of the formulation (i.e., a concentration of about 10 mM). Various embodiments are also provided in which any of the above-described formulations can additionally comprise benzyl alcohol, preferably in an amount of 0.45% (w/v) of the formulation.

In other aspects, the invention provides methods for administering propofol to a patient, and for either inducing or maintaining anesthesia in a patient. These methods involve administering any of the above described aqueous propofol formulations of the invention to the patient, until an effective amount of propofol (e.g., effective for inducing or maintaining anesthesia) has been administered.

5. BRIEF DESCRIPTION OF THE DRAWINGS

FIG. 1 illustrates exemplary data from HPLC analysis of aqueous propofol preparations described in the examples, infra, that are stored for a period of 1, 2, 3 and 4 weeks at 80° C. Data from HPLC analysis of the following formulations is shown: M841 (1% propofol, 8% poloxamer 188, 4% PEG-400 and 1% propylene glycol), M831 (1% propofol, 8% poloxamer 188, 3% PEG-400 and 1% propylene glycol) and M731 (1% propofol, 7% poloxamer 188, 3% PEG-400 and 1% propylene glycol). All samples contain citric acid (2 mg/ml) and benzyl alcohol (0.45%). Percentages of different excipients and other ingredients are in weight/volume.

FIGS. 2A-2B illustrate data from exemplary HPLC analysis of aqueous propofol preparations referred to in the examples, infra, as M831 (1% propofol, 8% poloxamer 188, 3% PEG-400 and 1% propylene glycol) that are stored at 80° C. under a variety of different pH conditions. FIG. 2A shows data from samples stored at pH 5.0, 6.0 and 7.0 for 1, 2, 3 and 4 weeks. FIG. 2B shows data from samples stored at pH 6.0, 6.2, 6.4, 6.5 and 6.6. All samples contain 0.45% benzyl alcohol and 2 mg/ml citric acid. Percentages of different excipients and other ingredients are in weight/volume.

FIG. 3 illustrates data from exemplary HPLC analysis of aqueous propofol preparations referred to in the examples, infra, as M831 (1% propofol, 8% poloxamer 188, 3% PEG-400 and 1% propylene glycol) stored at 80° C. and containing various concentrations of citric acid (0.5, 1 and 2 mg/ml). All samples contain 0.45% benzyl alcohol. Percentages of different excipients and other ingredients are in weight/volume.

FIG. 4 illustrates data from exemplary HPLC analysis of aqueous propofol preparations described in the examples, infra, and referred to as M831 and M830. Samples are analyzed after storage at 80° C., pH 5.0 for 0, 1, 2 and 3 weeks. The extent of propofol degradation in these samples is estimated from the are under elution curves for the particular impurity 3,3',5,5'-tetraisopropyl-4,4'-dihydroxybiphenyl (Impurity E) and by estimating the total impurity level of the preparations. M831 (1% propofol, 8% poloxamer 188, 3% PEG-400 and 1% propylene glycol, 0.45% benzyl alcohol and 2 mg/ml citric acid), M830 (1% propofol, 8% poloxamer 188, 3% PEG-400 and 0% propylene glycol, 0.45% benzyl alcohol and 2 mg/ml citric acid). Percentages of different excipients and other ingredients are in weight/volume.

FIG. 5 illustrates the preferred chemical structure of 2,6-diisopropylphenol (Formula I), which is also known as propofol. In propofol, R is a hydrogen (H). Formulas (II) through (VII) should chemical structures for other chemical moieties which can be substituted for R in some preferred derivatives and/or analogues of propofol.

6. DETAILED DESCRIPTION

The present invention relates to aqueous formulations of a lipophilic therapeutic agent. In preferred embodiments, the application relates to aqueous formulations of 2,6-diisopropylphenol, which is also commonly known as propofol. For convenience, formulations are described here as containing propofol as the active ingredient. However, formulations of the invention can actually contain any active ingredient or any combination of active ingredients. In preferred embodiments, a formulation of the invention will contain at least one active ingredient that is lipophilic and, consequently, not ordinarily normally used in aqueous formulations. For example, traditional formulations of propofol comprise oil or lipid emulsions since that compounds lipophilic nature has made it difficult to store in homogenous, aqueous formulations.

Figure 5:
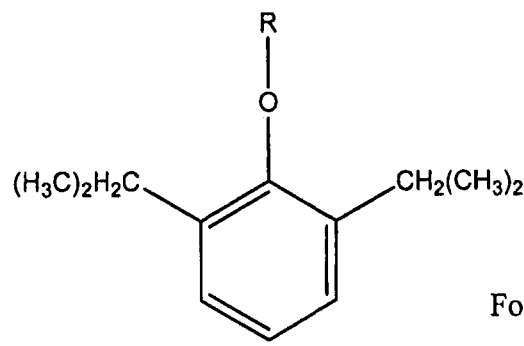
Figure 5:
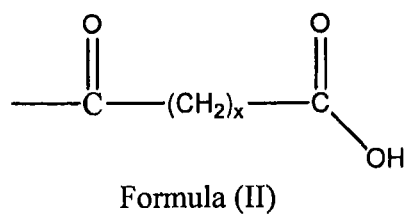
Figure 5:
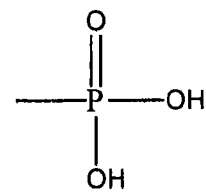
Figure 5:
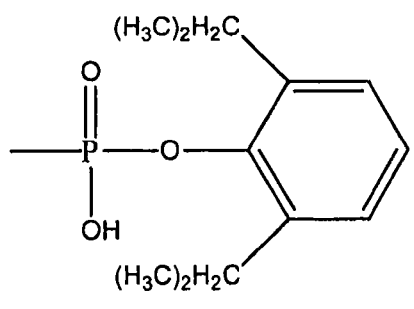
Figure 5:
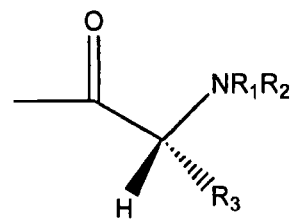
Figure 5:
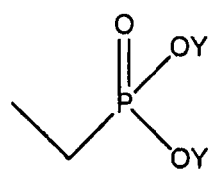
Figure 5:
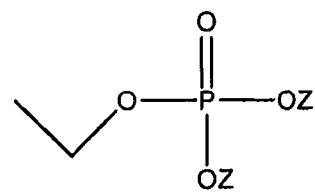
Figure 6:
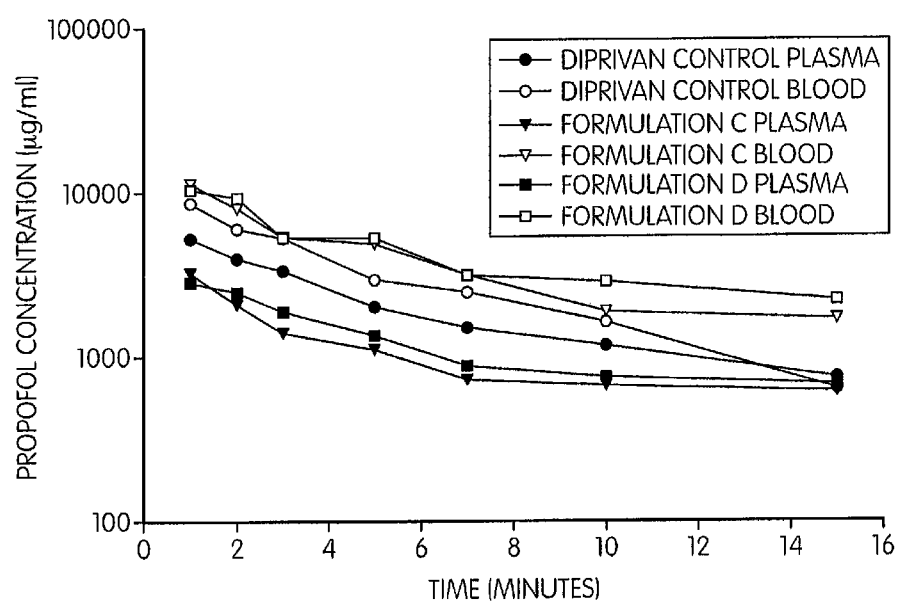
FIG. 6 shows the mean plasma and blood concentrations of propofol following administration of Formulations C and D and the Diprivan Emulsion control to the male rats.
Figure 7:
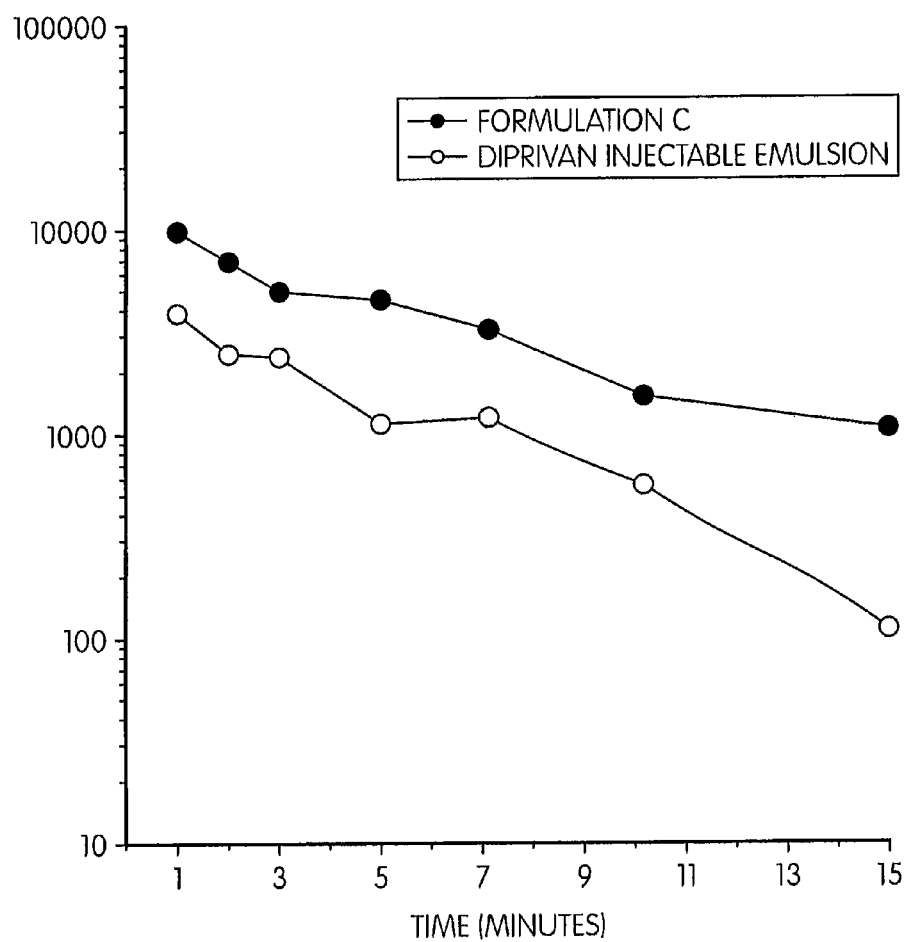
FIG. 7 shows mean predicted propofol concentrations in red blood cells (RBC) versus time following single intravenous doses (10 mg/kg) of Formulation C and Diprivan® Injectable Emulsion in male rats.

Propofol is understood to have the chemical structure of Formula (I) set forth in FIG. 5, where the moiety R is H. However, derivatives and analogues of propofol are also known and can be used in formulations of the present invention. Hence, the terms "2,6-diisopropylphenol" and "propofol," when used to describe the present invention, refer to the compound set forth in Formula (I) of FIG. 5 as well as to derivatives, analogues thereof. The terms "2,6-diisopropylphenol" and "propofol" also refer, in the context of the present invention, to pharmaceutically acceptable salts of propofol, its derivatives and analogues.

Examples of propofol analogues and derivatives that can be used in the present invention include compounds having the chemical structure set forth in Formula I (FIG. 5) where the moiety R has the chemical structure set forth in any of Formulas (II), (III), (IV), (V), (VI) and (VII) in FIG. 5. Preferred propofol analogues and derivatives include compounds of Formula (I) in which R has the formula set forth in Formula (II), where x is 2 and the propofol analogue is a hemisuccinate ester of propofol. As another example, R can have the chemical structure set forth in Formula (II), where x is 4 and the propofol analogue is a hemiadipate ester of propofol. Alternatively, R can have the chemical structure set forth in Formula (V), where $R_1$, $R_2$, and $R_3$ can be either the same or different chemical moieties and are independently selected from the group consisting of hydrogen, an alkyl, an alkenyl, an alkynyl, an alkoxy, an allenyl, an aryl, an aralkyl, or a halo or halogen. These moieties (i.e., $R_1$, $R_2$ and $R_3$) can be substituted or heteroatom containing. Alternatively, R can have the chemical structure set forth in Formula (VI) where Y is a phosphono protecting group which can be benzyl, t-butyl, or an allyl group. In other embodiments R can have the chemical structure set forth in Formula (VII) where Z is hydrogen or a metal or amine that forms pharmaceutically acceptable salts.

Pharmaceutically acceptable salts include all pharmaceutically acceptable salts of propofol or any of its derivatives or analogues. Hence, "pharmaceutically acceptable salts" include those salts of propofol, its derivatives or analogues that retain the biological effectiveness and properties of the free acids or free basis and that are not otherwise unacceptable for pharmaceutical use. Pharmaceutically acceptable salts of propofol derivatives include, for example, salts of acidic or basic groups which may be present in a propofol derivative. Derivatives of propofol that are basic in nature are capable of forming a wide variety of salts with various inorganic and organic acids. The acids that can be used to prepare pharmaceutically acceptable acid addition salts of such basic compounds are those that form non-toxic acid addition salts; i.e., salts containing pharmacologically acceptable anions such as chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, bentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Derivatives of propofol that include an amino moiety can also form pharmaceutically acceptable salts with various amino acids, in addition to the acids mentioned above. Derivatives of propofol that are acidic in nature are capable of forming a wide variety of salts with various inorganic and organic bases. Suitable base salts are formed from bases that donate cations to form non-toxic salts. Suitable cations include, but are not limited to, sodium, aluminum, calcium, lithium, magnesium, potassium, zinc, and diethanolamine salts. A more comprehensive review of pharmaceutically acceptable salts that can also be used in the present invention is provided by Berge et al. (*J. Pharm. Sci.* (1977) 66:1-19).

6.1. Propofol Formulations

The terms "composition" and "formulation" are used interchangeably herein and refer to mixtures that comprise propofol (as an active ingredient) and at least one excipient. Preferred formulations of the invention comprise propofol and at least two excipients, which are preferably a block copolymer and a polyethylene glycol (PEG). The terms "excipient" and "additive" are used interchangeably to describe the present invention, and refer to any compound contained in a formulation other than its primary activity ingredient (i.e., other than propofol) or water. Excipients can be inert or they can chemically or physically affect other composition components. In addition, an excipient or additive may have other properties of its own, for example, as a stabilizer or antimicrobial agent. Excipients can include, but are not limited to, surface active agents (for example, surfactants, emulsifiers, detergents, binders and wetting agents), salts, polymers, solvents, antimicrobials, preservatives, fillers, diagnostic agents, sugars, alcohols, acids, bases and buffers.

It is noted that exemplary, preferred amounts or ranges of amounts for propofol, excipients and various other ingredients in the formulations of this invention are provided throughout the description of this invention and its various embodiments. However, it will be appreciated by those skilled in the art that the precise amount of an ingredient used in not critical for practicing the invention. Rather, the amount specified for any ingredient in the description of this invention is merely approximate. Formulations containing about the same amount of a particular ingredient can also be used, even when the words "about" and/or "approximate" are not used here to describe the preferred amount of that ingredient. Generally, the amount used can be within 25% of an amount specified herein, although the amount used is more preferably within 15%, 10%, 5%, 2% or 1% of the amount specified.

In another embodiment, the composition comprises 2,6-diisopropylphenol, polyethylene glycol 400, poloxamer 188 and propylene glycol. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 0.5 to about 25%, about 0.5 to 15%, about 0.5 to 10%, about 0.5 to 8%, or about 0.5 to about 5% (w/v) propylene glycol, for example, about 0.5 to about 3% or about 0.5 to about 2% (w/v) propylene glycol; (d) about 1 to about 25%, about 1 to 15%, about 4 to 12%, about 5 to 10%, or about 6 to about 8% (w/v) poloxamer 188, for example, about 5 to about 9% or about 6 to about 7% (w/v) poloxamer 188; and (e) water. Optionally, benzyl alcohol may be added to this composition in concentrations up to 5%, up to 4%, up to 3%, up to 2%, up to 1% or up to 0.5%.

In other embodiments, the composition consists essentially of:

(1) water, 2,6-diisopropylphenol, poloxamer 188, polyethylene glycol 400, propylene glycol, optionally, a tonicity modifier, and, optionally, a pH modifier, or stabilizer (e.g., antioxidant such as cysteine, chelating agent such as EDTA, or other such as citric acid);

(2) water, 2,6-diisopropylphenol, poloxamer 188, polyethylene glycol 400, propylene glycol, and, optionally, citric acid or a salt thereof; or (3) water, 2,6-diisopropylphenol, poloxamer 188, polyethylene glycol 400, propylene glycol, optionally, citric acid or a salt thereof, and, optionally, a tonicity modifier.

(4) water, 2,6-diisopropylphenol at about 1% (w/v), poloxamer 188 at about 8% (w/v), polyethylene glycol 400 at about 4% (w/v), and propylene glycol at about 1% (w/v).

(5) water, 2,6-diisopropylphenol at about 1% (w/v), poloxamer 188 at about 6% (w/v), polyethylene glycol 400 at about 6% (w/v), and propylene glycol at about 1% (w/v).

(6) water, 2,6-diisopropylphenol at about 1% (w/v), poloxamer 188 at about 6% (w/v), polyethylene glycol 400 at about 4% (w/v), and propylene glycol at about 2% (w/v).

(7) water, 2,6-diisopropylphenol at about 1% (w/v), poloxamer 188 at about 8% (w/v), polyethylene glycol 400 at about 3% (w/v), and propylene glycol at about 1% (w/v).

(8) water, 2,6-diisopropylphenol at about 1% (w/v), poloxamer 188 at about 7% (w/v), polyethylene glycol 400 at about 4% (w/v), and propylene glycol at about 1% (w/v).

(9) water, 2,6-diisopropylphenol at about 1% (w/v), poloxamer 188 at about 7% (w/v), polyethylene glycol 400 at about 3% (w/v), and propylene glycol at about 1% (w/v).

(10) water, 2,6-diisopropylphenol at about 1% (w/v), poloxamer 188 at about 6% (w/v), polyethylene glycol 400 at about 4% (w/v), and propylene glycol at about 1% (w/v).

(11) water, 2,6-diisopropylphenol at about 1% (w/v), poloxamer 188 at about 8% (w/v), polyethylene glycol 400 at about 2% (w/v), and propylene glycol at about 1% (w/v).

In another embodiment, the composition comprises 2,6-diisopropylphenol, polyethylene glycol 400, poloxamer 188, propylene glycol, and citric acid. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 0.5 to about 25%, about 0.5 to 15%, about 0.5 to 10%, about 0.5 to 8%, or about 0.5 to about 5% (w/v) propylene glycol, for example, about 0.5 to about 3% or about 0.5 to about 2% (w/v) propylene glycol; (d) about 1 to about 25%, about 1 to 15%, about 4 to 12%, about 5 to 10%, or about 6 to about 8% (w/v) poloxamer 188, for example, about 5 to about 9% or about 6 to about 7% (w/v) poloxamer 188; (e) about 0.5 to 1% citric acid, about 0.5 to 4% citric acid, about 1 to 3% citric acid, about 2 to 5% citric acid, about 1 to 2% citric acid, and (f) water. Optionally, benzyl alcohol may be added to this composition in concentrations up to 5%, up to 4%, up to 3%, up to 2%, up to 1% or up to 0.5%.

In another embodiment, the composition comprises 2,6-diisopropylphenol, polyethylene glycol 400, and poloxamer 188. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 1 to about 25%, about 1 to 15%, about 4 to 12%, about 5 to 10%, or about 6 to about 8% (w/v) poloxamer 188, for example, about 5 to about 9% or about 6 to about 7% (w/v) poloxamer 188; and (e) water. Optionally, benzyl alcohol may be added to this composition in concentrations up to 5%, up to 4%, up to 3%, up to 2%, up to 1% or up to 0.5%.

In other embodiments, the composition consists essentially of:

(1) water, 2,6-diisopropylphenol, poloxamer 188, polyethylene glycol 400, optionally, a tonicity modifier, and, optionally, a pH modifier, or stabilizer (e.g., antioxidant such as cysteine, chelating agent such as EDTA, or other such as citric acid;

(2) water, 2,6-diisopropylphenol, poloxamer 188, polyethylene glycol 400, and, optionally, citric acid or a salt thereof; or (3) water, 2,6-diisopropylphenol, poloxamer 188, polyethylene glycol 400, optionally, citric acid or a salt thereof, and, optionally, a tonicity modifier.

(4) water, 2,6-diisopropylphenol at about 1% (w/v), poloxamer 188 at about 8% (w/v), and polyethylene glycol 400 at about 4% (w/v).

(5) water, 2,6-diisopropylphenol at about 1% (w/v), poloxamer 188 at about 8% (w/v), and polyethylene glycol 400 at about 3% (w/v).

(6) water, 2,6-diisopropylphenol at about 1% (w/v), poloxamer 188 at about 7% (w/v), and polyethylene glycol 400 at about 4% (w/v).

(7) water, 2,6-diisopropylphenol at about 1% (w/v), poloxamer 188 at about 7% (w/v), and polyethylene glycol 400 at about 3% (w/v).

(8) water, 2,6-diisopropylphenol at about 1% (w/v), poloxamer 188 at about 6% (w/v), and polyethylene glycol 400 at about 6% (w/v).

(9) water, 2,6-diisopropylphenol at about 1% (w/v), poloxamer 188 at about 9% (w/v), and polyethylene glycol 400 at about 2% (w/v).

Another composition comprises 2,6-diisopropylphenol, polyethylene glycol 400, and a purified poloxamer with an average molecular weight range between about 7600 and 9500. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 1 to about 25%, about 1 to 15%, about 4 to 12%, about 5 to 10%, or about 6 to about 8% (w/v) purified poloxamer with an average molecular weight range between about 7600 and 9500, for example, about 5 to about 9% or about 6 to about 7% (w/v) purified poloxamer with an average molecular weight range between about 7600 and 9500; and (e) water.

Another composition comprises 2,6-diisopropylphenol, polyethylene glycol 400, and a purified poloxamer with an average molecular weight range between about 7600 and 9000. Another composition comprises 2,6-diisopropylphenol, polyethylene glycol 400, and a purified poloxamer with an average molecular weight range between about 8000 and 9000. Another composition comprises 2,6-diisopropylphenol, polyethylene glycol 400, and a purified poloxamer with an average molecular weight range between about 8000 and 8500.

In another embodiment, the composition comprises 2,6-diisopropylphenol, polyethylene glycol 400, a purified poloxamer with an average molecular weight range between about 7600 and 9500 and propylene glycol. This composition can comprise: (a) propofol as described above; (b) about 1 to about 25%, about 1 to 15%, about 2 to 10%, about 2 to 8%, or about 2 to about 6% (w/v) polyethylene glycol 400, for example, about 3 to about 6% or about 4 to about 6% (w/v) polyethylene glycol 400; (c) about 0.5 to about 25%, about 0.5 to 15%, about 0.5 to 10%, about 0.5 to 8%, or about 0.5 to about 5% (w/v) propylene glycol, for example, about 0.5 to about 3% or about 0.5 to about 2% (w/v) propylene glycol; (d)

about 1 to about 25%, about 1 to 15%, about 4 to 12%, about 5 to 10%, or about 6 to about 8% (w/v) purified poloxamer, for example, about 5 to about 9% or about 6 to about 7% (w/v) purified poloxamer; and (e) water.

In another embodiment, the composition comprises 2,6-diisopropylphenol, polyethylene glycol 400, a purified poloxamer with an average molecular weight range between about 7600 and 9000 and propylene glycol. In another embodiment, the composition comprises 2,6-diisopropylphenol, polyethylene glycol 400, a purified poloxamer with an average molecular weight range between about 8000 and 9000 and propylene glycol. In another embodiment, the composition comprises 2,6-diisopropylphenol, polyethylene glycol 400, a purified poloxamer with an average molecular weight range between about 8000 and 8500 and propylene glycol.

In yet another embodiment, the composition comprises polyethylene glycol (e.g., PEG-400) and poloxamer (e.g., Poloxamer 237). This composition can comprise (a) propofol as described above; (b) about 2 to about 30%, about 3 to about 20%, about 3 to 15%, about 3 to 12%, or about 3 to about 9% (w/v) PEG-400, for example, about 3 to about 7% or about 5 to about 7% (w/v) PEG-400; (c) about 1 to about 25%, about 1 to 15%, about 1 to 10%, about 1 to about 5%, or about 1 to about 3% (w/v) Poloxamer 237, for example, about 1 to about 2% or about 1.1 to about 1.5% (w/v) Poloxamer 237; and (d) water.

In alternative embodiments, the composition also consist essentially of:

(1) water, 2,6-diisopropylphenol, polyethylene glycol 400, Poloxamer 237, optionally, a tonicity modifier, and optionally, a pH modifier;

(2) water, 2,6-diisopropylphenol, polyethylene glycol 400, Poloxamer 237, optionally, and, optionally, citric acid or a salt thereof; or (3) water, 2,6-diisopropylphenol, polyethylene glycol 400, Poloxamer 237, optionally, citric acid or a salt thereof, and, optionally, a tonicity modifier.

Another composition of the invention comprises polysorbate (e.g., polyoxyethylene 20 sorbitan monooleate), propylene glycol, polyethylene glycol (e.g., PEG-400), and poloxamer (e.g., Poloxamer 188). This composition can comprise (a) propofol as described above; (b) about 0.5 to about 25%, about 0.5 to 15%, about 1 to 10%, or about 1 to about 5% (w/v) polyoxyethylene 20 sorbitan monooleate, for example, about 1 to about 3% or about 1 to about 2% (w/v) polyoxyethylene 20 sorbitan monooleate; (c) about 0.5 to about 25%, about 0.5 to 15%, about 0.5 to 10%, about 0.5 to about 5%, about 0.5 to about 3%, about 0.5 to about 2%, about 0.5 to about 1%, or about 1 to about 3% (w/v) propylene glycol, for example, about 1 to about 2% (w/v) propylene glycol; (d) about 1 to about 30%, about 1 to about 20%, about 2 to 15%, or about 2 to about 8% (w/v) PEG-400, for example, about 3 to about 6% or about 4 to about 5% (w/v) PEG-400; (e) about 1 to about 25%, about 1 to 15%, about 2 to 10%, or about 2 to about 8% (w/v) Poloxamer 188, for example, about 3 to about 7% or about 4.5 to about 5.5% (w/v) Poloxamer 188; and (f) water. In some embodiments, this composition further comprises citric acid or a salt thereof. Citric acid can be present in the compositions in concentrations of at least about 0.05 percent (w/v) such as about 0.05 to about 5%, about 0.1 to about 3%, about 0.1 to about 1% (w/v), for example, about 0.1 to about 0.5% or about 0.1 to about 0.2%, or 0.15% (w/v).

These compositions may alternatively consist essentially of:

(1) water, 2,6-diisopropylphenol, polyoxyethylene 20 sorbitan monooleate, propylene glycol, polyethylene glycol 400, Poloxamer 188, optionally, a tonicity modifier, and optionally, a pH modifier;

(2) water, 2,6-diisopropylphenol, polyoxyethylene 20 sorbitan monooleate, propylene glycol, polyethylene glycol 400, Poloxamer 188, and, optionally, citric acid or a salt thereof; or (3) water, 2,6-diisopropylphenol, polyoxyethylene 20 sorbitan monooleate, propylene glycol, polyethylene glycol 400, Poloxamer 188, optionally, citric acid or a salt thereof, and, optionally, a tonicity modifier.

In some embodiments, the composition contains benzyl alcohol. In some compositions benzyl alcohol may provide added antimicrobial activity. Benzyl alcohol concentrations can be below 5% w/v, below 4% w/v, below 3% w/v, below 2% w/v, below 1% w/v, below 0.5% w/v, or at 0.45% w/v.

As noted above, formulations of the present invention preferably comprise at least two excipients which are present, along with propofol, in a homogenous aqueous phase. In preferred embodiments, the two excipients are: (1) a block co-polymer, and (2) a polyethylene glycol (PEG). In particular, it has been discovered that the inclusion of a small amount (e.g., between 2 and 6%) of a polyethylene glycol with a block co-polymer surfactant produces a synergistic affect, greatly increasing the amount of a lipophilic active ingredient such as propofol that can be homogenously suspended in an aqueous medium. As a result, the total amount of excipients used in a formulation of the invention is significantly reduced compared to amounts that have been traditionally used in propofol preparations.

Generally, the concentration of excipients should be as low as possible, to minimize the risk of undesired excipient effects (see, for instance, Blonder et al., Life Sci. (1999) 65:PL261-266; and Johnston et al., Cardiovasc. Pharmacol. (1999) 34:831-842). In preferred embodiments, therefore, the concentration of excipients in a formulation is less than about 50%, and is more preferably less than about 40%, less than about 30%, less than about 25%, less than about 20%, less than about 15% or even less than about 10% (w/v).

For example, in preferred embodiments that total amount of block co-polymer in a formulation is less than about 10% (w/v) of the formulation, and is more preferably between about 5 and 10% (w/v). In particularly preferred embodiments, the total amount of block co-polymer is a formulation of the invention is between about 6 and 8% (w/v) of the formulation.

Preferably, the block co-polymer used in a formulation of the present invention is a "poloxamer". Poloxamers are poly (a-oxyethylene-b-oxypropylene-a-oxyethylene) triblock copolymers that are commonly used as surfactants and are generally regarded as non-toxic. The solubility of poloxamers in water is generally good. However, the properties of individual poloxamers can vary substantially. Poloxamer copolymers can be obtained from BASF Corporation (Parsippany, N.J.) under the Pluronic® registered tradename. Preferred poloxamers that can be used in formulations of the invention include poloxamer 124 (P124), poloxamer 188 (P188), poloxamer 237 (P237), poloxamer 338 (P338) and poloxamer 407 (P407), although any poloxamer can be used. In addition poloxamers as described in U.S. Pat. No. 5,990,241 can also be used in formulations of the invention. In preferred embodiments, a poloxamer used in formulations of the present invention is one approved (for example, by the U.S. Food and Drug Administration) for use in pharmaceutical preparations (e.g., for administration to humans) and, in particular approved for use in intravenous and/or other injectable formulations. At present, only poloxamer 188 is believed to be approved for such uses in the United States. Hence, poloxamer 188 is particularly preferred in formulations of the present invention at this time. However, other poloxamers, such as P237, may actually be superior solubilizers of lipophilic compounds such as propofol. It is therefore expected that such other poloxamer compounds will be preferred for use in the present invention should they also be approved for use in injectable preparations, e.g., for intravenous administration.

Purified poloxamers with narrower ranges of polymer molecular weight composition can be selected for a composition of this invention. Narrower ranges (e.g. compared to commercially available poloxamer 188 or poloxamer 237) of purified poloxamer may have a polydispersity value of, for example, 1.01, 1.02, 1.04, 1.05, 1.1, 1.3, 1.5, 2, 3, or 4. In some embodiments, the polydispersity value of a purified poloxamer is between 5 and 1, between 4 and 1, between 3 and 1, between 2 and 1, between 1.5 and 1, between 1.3 and 1, between 1.2 and 1 or between 1.1 and 1. In some embodiments, a purified poloxamer contains at least 50%, at least 60%, at least 70%, at least 80%, at least 90%, or at least 95% of polymers with a molecular weight between 2000 and 15,000. In some embodiments, a purified poloxamer contains at least 50%, at least 60%, at least 70%, at least 80%, at least 90%, or at least 95% of polymers with a molecular weight between 3000 and 14,000. In some embodiments, a purified poloxamer contains at least 50%, at least 60%, at least 70%, at least 80%, at least 90%, or at least 95% of polymers with a molecular weight between 4000 and 13,000. In some embodiments, a purified poloxamer contains at least 50%, at least 60%, at least 70%, at least 80%, at least 90%, or at least 95% of polymers with a molecular weight between 5000 and 12,000. In some embodiments, a purified poloxamer contains at least 50%, at least 60%, at least 70%, at least 80%, at least 90%, or at least 95% of polymers with a molecular weight between 5000 and 11,000. In some embodiments, a purified poloxamer contains at least 50%, at least 60%, at least 70%, at least 80%, at least 90%, or at least 95% of polymers with a molecular weight between 6000 and 10000. In some embodiments, a purified poloxamer contains at least 50%, at least 60%, at least 70%, at least 80%, at least 90%, or at least 95% of polymers with a molecular weight between 7000 and 9000. In some embodiments, a purified poloxamer contains at least 50%, at least 60%, at least 70%, at least 80%, at least 90%, or at least 95% of polymers with a molecular weight between 7500 and 8500. In some embodiments, a purified poloxamer contains at least 50%, at least 60%, at least 70%, at least 80%, at least 90%, or at least 95% of polymers with a molecular weight between 8000 and 9500.

Preferred formulations of the invention also comprise a polyethylene glycol (PEG) in combination with the poloxamer or other block co-polymer. In particular, it has been discovered that the combination of PEG with block co-polymers greatly increases the amount of propofol that can be held in an aqueous phase suspension, solution or emulsion. Consequently, aqueous formulations of propofol that are suitable for injection can now be made without the use of oil or lipid based emulsions. Preferably, the amount of PEG in a formulation of the invention is not greater than about 10% (w/v) of the formulation, and more preferably is not greater than about 5% (w/v) of the formulation. In various embodiments, however, the total amount of PEG in a propofol formulation of the invention can be as high at 15%, 10%, 9%, 8%, 7%, 6%, 5%, 4%, 3%, 2% or 1% (w/v) of the formulation. Particularly preferred formulations of the invention comprises between about 2% and about 6% (w/v) PEG and, more preferably, between about 2 and 4% PEG. Polyethylene glycols having a molecular weight of about 200 (i.e., PEG-200), 300 (PEG-300), 400 (PEG-400), 600 (PEG-600), 800 (PEG-800) or 1000 (PEG-1000) can be used. However, the use of PEG-400 is preferred.

It has been discovered that, by combining PEG with a block co-polymer surfactant such as a poloxamer, it is possible to greatly increase the amount of propofol or other lipophilic active ingredient that is held in a homogeneous, aqueous phase (e.g., in a solution, suspension or emulsion) without requiring the use of traditional oil or lipid excipients. Hence, formulations of the present invention can also contain higher levels of propofol than traditional formulations. Thus, for example, formulations of the present invention can comprise an amount of propofol as high as 10% (w/v) of the formulation, although amount of 5% (w/v) or less are generally more preferred. Such higher amounts of propofol will require the administration of smaller volumes to achieve the same therapeutic effect, and are generally more cumbersome or difficult to safely administer. Hence, more preferred formulations of the invention comprise propofol in an amount that is not greater than about 2% (w/v) of the formulation. Preferred formulations comprise propofol in an amount between 0.5 and 2% (w/v) of the formulation, and more preferably between 1 and 2% (w/v) of the formulation, with amount of about 1% (w/v) being particularly preferred.

Propofol compositions of the present invention can further comprise other ingredients, that are not normally considered excipients and which may also be biologically active. For example, a propofol composition of the invention may comprise one or more additional anesthetic and/or antioxidative agents. Alternatively, propofol formulations of the invention may be co-administered with one or more such additional active agents.

Pharmaceutical compositions that are intended for application to delicate membranes of the body are commonly adjusted to approximately the same tonicity (i.e., isotonicity) as that of the body fluids. Isotonic compositions are those that cause minimal swelling or contraction of the tissues with which they come in contact, and produce little or no discomfort when instilled in body tissues. Preferably, the propofol compositions are substantially isotonic. The compositions may additionally comprise one or more tonicity modifiers. Examples of tonicity modifiers include, but are not limited to, lactose, dextrose, dextrose anhydrous, mannitol, sodium chloride, potassium chloride, propylene glycol and glycerol.

The use of propylene glycol as an isotonic agent in the present invention is particularly preferred. Hence, preferred formulations of the invention comprise propylene glycol in addition to the block co-polymer and polyethylene glycol excipients described supra. Generally, the amount of propylene glycol in a formulation of the present invention will not be greater than about 5% (w/v) of the formulation, with amounts less than or equal to about 2% being preferred. Preferred formulations of the invention comprise propylene glycol in an amount of about 0%, 1% or 2%.

Although not necessary to practice the present invention, preferred aqueous propofol compositions can also comprise an optional antimicrobial agent. For example, a formulation of the invention can comprise disodium edetate, metabisulfate, or a preservative such as benzyl alcohol, or an antioxidant such as cysteine or a salt thereof to retard the growth of microorganisms. In this embodiment, the compositions of the present invention comprise a microbiostatic, microbicidal, preservative, or antioxidant (e.g., cysteine or a salt thereof) in a concentration sufficient to exhibit microbiostatic or microbicidal activity against those microorganisms most likely to contaminate the propofol compositions. A further embodiment includes a sterile pharmaceutical composition for parenteral administration which comprises an aqueous solution of propofol, and which further optionally comprises a microbiostatic, microbicidal, preservative, or antioxidant such as cystein (or a salt thereof), EDTA, benzyl alcohol, or metabisulfite, and wherein said aqueous propofol solution is sufficient to prevent no more than a 10-fold increase in growth, or will support no more than a 10-fold increase in growth, of each of Staphylococcus aureus ATCC 6538, Escherichia coli ATCC 8739, Pseudomonas aeruginosa ATCC 9027 and Candida albicans ATCC 10231 for at least 24 hours as measured by a test wherein a washed suspension of each said organism is added to a separate aliquot of said composition at approximately 50 colony forming units per ml, at a temperature in the range 20° C. to 25° C., whereafter said aliquots are incubated at 20° C. to 25° C. for 24 hours and thereafter tested for viable counts of said organism. Another embodiment includes a method for producing anaesthesia in a warm-blooded animal which comprises parenterally administering to said animal in need thereof an anaesthetically effective amount of a sterile pharmaceutical composition which comprises an aqueous solution of propofol, and which composition further optionally comprises a microbiostatic, microbicidal, preservative, or antioxidant such as cystein (or a salt thereof), EDTA, or metabisulfite, and wherein said aqueous propofol solution is sufficient to prevent no more than a 10-fold increase in growth, or will support no more than a 10-fold increase in growth, of each of Staphylococcus aureus ATCC 6538, Escherichia coli ATCC 8739, Pseudomonas aeruginosa ATCC 9027 and Candida albicans ATCC 10231 for at least 24 hours as measured by a test wherein a washed suspension of each said organism is added to a separate aliquot of said composition at approximately 50 colony forming units per ml, at a temperature in the range 20° C. to 25° C., whereafter said aliquots are incubated at 20° C. to 25° C. for 24 hours and thereafter tested for viable counts of said organism.

In addition, preferred formulations of the invention can also comprise citric acid or a salt thereof. Without being held to any particular theory, Applicants believe that citric acid or a salt thereof in the compositions of the present invention exhibits antioxidant and/or chelating properties. Applicants have discovered that compositions comprising citric acid or a salt thereof possess an unexpectedly high degree of propofol stability. Also, Applicants have discovered that compositions comprising ascorbic acid or salts thereof unexpectedly display significant propofol degradation. Thus, citric acid or a salt thereof is added to the compositions of the present invention for its favorable effects including but not limited to modifying pH and/or providing or enhancing (a) antioxidant characteristics, (b) chelating effects of the composition, and/or (c) stability of the excipient(s) or the active agent(s) such as, for example, the propofol compound. Citric acid or a salt thereof is preferably present in a concentration sufficient to optimize and balance the desired pH and/or the desired antioxidant or chelating properties. In one aspect, the present invention is directed to propofol containing compositions wherein the composition further comprises citric acid or a salt or salts of citric acid in a concentration of at least about 0.05 percent (w/v), in particular, as at least about 0.1 percent (w/v). For example, citric acid or one or more salts thereof can be present in a formulation of the present invention in an amount between about 0.05 and 3%, with amounts between about 0.05 and 0.2% being particularly preferred. In preferred embodiments, citric acid can be present in a formulation of the invention at a concentration of between about 2.5 and 15 mM, with concentrations of about 10 mM (i.e., about 2 mg/ml) being particularly preferred.

In some embodiments, excipients are present in the propofol containing compositions in the lowest concentrations that will support the formation of a stable composition (e.g., a physically, thermodynamically, and/or chemically stable composition). Keeping excipient concentrations as low as possible helps to minimize the risk of undesired excipient effects. The propofol containing compositions are preferably free of preservatives and/or anti-microbials. Preferably, the compositions are also sterile and pyrogen-free.

Preferred formulations of the invention are also substantially free of lipid components such as lecithin, castor oil, soybean oil, phospholipids, fatty acids, triablycerols, etc, that are commonly used in traditional propofol formulations. As such, the preferred formulations of this invention do not support microbial growth, or the rate of microbial growth in these compositions is significantly slower when compared to such growth in conventional, lipid-containing formulations.

The term "substantially free," as used herein, refers to compositions that contain the indicated component in only minor amounts if at all. For example, a composition of the invention can be "substantially free" of an ingredient and still contain trace amounts of that component, e.g., as a degradation process. Preferably, however, compositions of the invention that are "substantially free" of a certain component will contain that component only a minimal concentration, for example, of less than about 3%, more preferably less than about 1%, less than about 0.5%, or less than about 0.1%. Even more preferably, a composition that is said to be "substantially free" of some component will contain less than about 0.05% (w/v) or even less than about 0.01% (w/v) of that component. In fact, particularly preferred compositions that are "substantially free" of a particular component will not contain measurable or detectable amounts of that component.

Preferred compositions of the invention have substantially reduced concentrations of excipients that promote and/or facilitate microbial growth compared to traditional emulsions and other formulations of propofol. Indeed, particularly preferred propofol formulations of the invention are substantially free of and/or do not contain any such excipients. These include excipients, such as lipids and/or oils, that are traditionally used to solvate or suspend propofol in aqueous formulations. In addition, compositions of the invention are preferably free of or are substantially free of esters of medium or long chain fatty acids (e.g., about $C_6$ to about $C_{25}$ fatty acids) such as glyceryl esters of medium or long chain fatty acids (e.g., mono- di- or traicylglycerols). Preferably, the compositions of the invention are also substantially free of triaglycerols such as, for example, those contained in vegetable oils (e.g., soybean, castor, sunflower, and artichoke oils). In another embodiment, the compositions are free of or are substantially free of phospholipids (e.g., naturally occurring phospholipids or phospholipids that are synthetically produced and modified).

Examples of some preferred formulations in the present invention are described in the Examples, infra, including the formulations set forth in Table I of those examples. Of these, the formulation identified as M831 (1% propofol, 8% poloxamer 188, 3% PEG-400, and 1% propylene glycol) is particularly preferred. Any of these or other formulations of the invention may additionally comprise, e.g., a preservative such as citric acid (as described above) and/or an antimicrobial agent such as benzyl alcohol (as also described above). Preferred formulations of the invention do comprise citric acid, preferably at a concentration of between about 2.5 and 15 mM and with a concentration of 20 mg per 10 milliliters of formulation (i.e., about 10 mM) being particularly preferred. Preferred formulations of the invention also contain benzyl alcohol in addition to the other, above-described excipients. Preferably, benzyl alcohol is present as an antimicrobial agent and in an amount of about 0.45% (w/v) of the formulation.

Aqueous formulations of the invention are preferably clear, transparent and sterile, or they can be readily sterilized by conventional and routine methods such as ultrafiltration. Moreover, formulations of the invention are both chemically and physically stable over a wide range of environmental conditions, including a wide range of different temperature and pH conditions.

Compositions of the present invention can also be characterized, inter alia, by their macroscale homogeneity. Macroscale homogenous compositions are characterized by a lack of distinguishable phase separation. Conventional propofol emulsions are milky white in appearance, which indicates that presence of two or more distinct phases such as oil droplets suspended in an aqueous phase (i.e., water). The oil droplets in such emulsions, which are typically about one micron in size, scatter light giving rise to their milky or "hazy" appearance.

By contrast, compositions of the present invention are preferably clear or transparent to the naked eye. Without being limited to any particular theory or mechanism of action, it is believed that this visual clarity indicates that propofol in such compositions is suspended in particles that are substantially smaller than in conventional formulations, e.g., oil-in-water emulsions, of propofol. For instance, the examples, infra, describe dynamic light scattering and/or other measurements indicating the presence of nano-scale particles in compositions of the present invention, such that light scattering is minimized and the system appears as a homogeneous composition.

It is believed that compositions that maintain clarity under visual inspection over time (including propofol formulations of the present invention) possess a greater degree of thermodynamic stability than that possessed by conventional emulsions. Generally, solutions or mixtures having a high degree of thermodynamic stability tend to maintain particles or particle agglomeration in solution or to preserve their suspension in a liquid over significant periods of time and/or under conditions that do not typically favor continued solvation or suspension. For example, solutions or suspensions that are not thermodynamically favored will typically exhibit a separation of phases such as a precipitation of solute or suspended matter. Environmental conditions can be selected to maintain thermodynamically disfavored states over longer periods of time. For example, refrigeration is often used to help maintain the suspension of particles in an emulsion.

Typically, compositions of the present invention maintain the solvation and/or suspension of their component ingredients over long periods of time (e.g., for at least as long as conventional oil-in-water propofol emulsions) and/or under conditions more unfavorable to thermodynamic stability (e.g., at higher temperatures and/or under harsher pH conditions). For example, compositions of the invention preferably exhibit visual clarity to the naked eye even when stored at elevated temperatures over extended periods of time. Phase separation of compositions can also be assessed microscopically, by light scattering or nephelometry, or by other suitable methods that are well known to those of ordinary skill in the art. For instance, and not by way of limitation, the examples, infra, describe experiments demonstrating that aqueous propofol formulations of the invention are stable for periods of four weeks or more, even when stored under very harsh environmental conditions, e.g., of elevated temperature (80° C.) and/or pH. However, it will be appreciated that formulations of the invention will remain stable for even greater periods of time, particularly when stored under more favorable conditions. For example, formulations of the invention are expected to remain stable for periods of up to 2 weeks, 4 weeks, 6 weeks, 8 weeks, 10 weeks, six months, eight months, ten months, twelve months, eighteen months or more. In fact, compositions of the invention can even be stored for periods of up to 1, 2, 3, 5, 10 or more years and still maintain their solvation or suspension, particularly if stored at a temperature between about 10 and 40° C. and more preferably at a temperature between about 15 and 25° C. Preferably, the compositions are also stored at a pH of about 5.0±0.5. Alternatively, compositions of the invention may also be refrigerated stored for the above-listed time periods or greater. Although compositions of the invention may become hazy (indicating a loss of suspension or solvation) when stored under such conditions, data presented in the examples, infra, demonstrate that this loss of suspension/solvation is reversible. Hence, compositions stored under such conditions can become clear and/or transparent again once equilibrated to room temperature, indicating resolution or resuspension of the lipophilic propofol component.

The compositions of the present invention can be characterized by the size of the particles (mean diameter) present in the composition. Without being held to any particular theory, it is believed that in some embodiments the particles contained in the compositions take the form of micelles of various sizes. Alternatively, it is believed that some compositions, or portions of compositions, take the form of micro- or nano-emulsions. The particle size, also herein referred to as the particle geometric size or particle geometric diameter, can be determined using any of the techniques known to those of skill in the art. For example, a Malvern Instruments Zetasizer can be used to determine the size of particles in a composition. The Zetasizer line of measurement systems uses the technique of Photon Correlation Spectroscopy (PCS) to measure submicron particle size. Particles dispersed in a fluid are in constant random motion, commonly referred to as Brownian motion. Photon Correlation Spectroscopy measures the speed of this motion, calculates the diffusion speed of the particles, and relates this to particle size using the Stokes-Einstein equation. One skilled in the art also may employ other suitable means to determine particle size.

In addition to Photon Correlation Spectroscopy (PCS), other methodologies relating to particle size analysis known to those skilled in the art can be employed including, but not limited to, microscopy (e.g., optical and electron), electrozone or photozone sensing, and other light scattering techniques (e.g., laser diffraction).

In some embodiments, the compositions have an average particle size (mean diameter) less than about 100 nanometers, between about 10 and about 100, between about 25 and about 90 nanometers, or between about 30 and about 75 nanometers. Compositions of the invention consist of particles having a geometric diameter of less than about 90, less than about 75 nanometers, less than about 65 nanometers, less than about 55 nanometers less than about 50 nanometers, less than about 45 nanometers, less than about 40 nanometers, less than about 35 nanometers, less than about 30 nanometers, less than about 25 nanometers, less than about 20 nanometers, less than about 15 nanometers, less than about 10 nanometers, less than about 5 nanometers, or less than about 1 nanometer. In some embodiments, the compositions have an average particle size of between about 50 and 250 nanometers, between about 50 and 150 nanometers, between about 150 and 250 nanometers, and between about 100 and 200 nanometers. In some compositions, all particles have a relatively similar particle size. A relatively similar particle size is defined as the particle size and consistency required of a pharmaceutical product to attain US Food and Drug Administration human drug approval. Optionally, compositions of the present invention are filtered to produce compositions comprising particles of desired sizes or average sizes. Methods for filtering such compositions are well known to those skilled in the art.

In some embodiments, the compositions of this invention have superior clinical benefits compared to currently marketed propofol formulations or other aqueous propofol formulations. Superior clinical benefits can include, but are not limited to, decreased lipid levels, faster onset of action, faster offset of action, decreased damage to red blood cells, and fewer side effects.

The compositions of the invention can be characterized by the chemical stability of the therapeutic, prophylactic or diagnostic agents that comprise the particles. The chemical stability of a constituent anesthetic agent can affect important characteristics of a pharmaceutical composition including shelf-life, proper storage conditions, acceptable environments for administration, biological compatibility, and effectiveness of the agent. Chemical stability can be assessed using techniques well known in the art. For example, assays to detect degradation information obtained from stress studies (e.g., products of acid and base hydrolysis, thermal degradation, photolysis, and oxidation) for both active ingredients and excipients are numerous. One example of a technique that can be used to assess chemical stability is reverse phase high performance liquid chromatography (HPLC).

The compositions of the invention do not exhibit substantial propofol degradation such as, for example, no more than about 5% or no more than about 3% loss of propofol potency at room temperature over a given study period. Alternatively, propofol degradation can be assessed by measuring propofol degradate concentrations such as, for example, quinone and dimer concentrations. In some embodiments, the compositions do not exhibit substantial increases in propofol degradates such as, for example, no more than about 0.05%, no more than about 0.1%, or no more than about 0.2% increase in propofol degradate concentration over a given study period. In a preferred embodiment, any single degradate does not exceed the International Conference on Harmonization (ICH) guidelines, unless specific qualification of that degradate has been performed. (See ICH Document Q3B).

In one embodiment, the compositions do not experience substantial propofol degradation for a period of at least about 6 months when stored refrigerated. Preferably, the compositions do not experience substantial propofol degradation for a period of at least about one year when stored refrigerated. Even more preferred, the compositions do not experience substantial propofol degradation for at least about 6 months, for at least about one year, or, most preferably, for at least about two years when stored at or below about room temperature.

The compositions of the present invention preferably have a physiologically neutral pH, such as between about 5 and about 9. The pH of the propofol containing compositions can be adjusted as necessary by, for example, the addition of a base or a salt thereof, for example, an alkali such as sodium hydroxide, potassium hydroxide, or the like. Alternatively, an acid or a salt thereof such as hydrochloric acid, citric acid, or the like can be used to adjust the pH of the compositions. The term "pH modifier," as used herein, refers to substances such as acids, bases, or salts thereof that are used to adjust the pH of a composition and that are well known to those skilled in the art.

In some embodiments, the stability of the compositions of this invention are sensitive to pH. In some compositions, propofol containing compositions have greater stability at a pH of about 5 to 6, at about 4.5 to 6.5, at about 4.5 to 5.5, at about 5 to 7.5 at about 6 to 7, or at about 6.5 to 7.5. The pH of the composition can be adjusted with a pharmaceutically acceptable acid or base to obtain a desired pH. In some embodiments, a specific pH can affect the composition stability or microbial growth.

6.2. Methods of Manufacture

The propofol containing compositions are preferably provided or administered as sterile pharmaceutical compositions. For example, the propofol containing compositions are administered substantially free of microorganisms. The preparation of sterile pharmaceutical compositions is well known to those experienced in the art. Sterile propofol containing compositions can be prepared using conventional techniques such as, for example, sterilization of final products or aseptic manufacture. In a preferred embodiment, the sterile compositions of the invention are substantially free of microorganisms for a longer period of time after opening than currently available propofol compositions such as Diprivan® Injectable Emulsion.

The compositions of the present invention can be provided in forms that possess desired propofol concentrations and are ready for direct administration to a patient. Alternatively, compositions can be provided in a concentrated form that requires dilution, for example, with water or an injectable solution, prior to administration. In the case of intravenous administration, the compositions can be admixed with diluents suitable for intravenous administration well known to those experienced in the art. Such diluents include water and injectable, aqueous sodium chloride and dextrose solutions. Due to the clear and homogenous character of the compositions of the invention, if further diluted, the resulting diluted compositions are generally also homogeneous and clear.

Compositions of the present invention can be formed by mixing 2,6-diisopropylphenol, one or more excipients, and water. Various methods of mixing the composition components are contemplated. Excipients can be mixed into the compositions as neat excipients or as excipients in water. Propofol can be mixed into at least one or more neat excipients or into at least one or more excipients in water. The 2,6-diisopropylphenol may be mixed with at least one or more excipients in water and then combined with either (1) at least one or more neat excipients or (2) with at least one or more excipients mixed in water. In a preferred embodiment, the excipients are mixed together, water is added with mixing, then propofol is added with mixing, and finally, additional water is optionally added to increase the mixture volume. Also preferred, excipients in water are mixed together, propofol is added with mixing, and finally, additional water is optionally added to increase the mixture volume. In most embodiments, propofol is added last.

The water used in the compositions of the present invention is preferably suitable for animal, including human, injection. The water should meet appropriate government and/or health care industry standards. Preferably, the water meets United States Pharmacopeia (USP) 23 standards for Pharmaceutical Grade Water for Injection. Normally, the water should contain no added substances.

Mixing may be performed by any of the various methods known in the art. A mixing apparatus may be batch or continuous. Examples of suitable mixing apparatuses include jet mixers, injectors, mixing nozzles, pumps, agitated line mixers, packed tubes, gas agitated vessels, and stirred vessels, among others. Mixing can be carried out at any temperature that does not substantially degrade the composition components. Typically, mixing is performed at or near room temperature. An advantage of practicing the present invention is the ease by which the compositions can be prepared compared with the methods, such as, for example, microfluidization techniques, often necessary to form propofol compositions, for example, conventional propofol emulsions.

The compositions can be provided, prepared, stored, or transported in any container suitable for maintaining sterility. The container can incorporate means for dispensing an aqueous composition such as, for example, a pierceable or removable seal. The compositions can be dispensed, for example, by extraction with a syringe or by pouring the composition directly into a device (e.g., a syringe, intravenous (IV) bag, or machine) for administration to a patient. Other means for providing, preparing, storing, transporting, and dispensing sterile pharmaceutical compositions are known to those skilled in the art.

In one embodiment, the compositions of the invention are manufactured, packaged, stored, or administered under an oxygen free atmosphere since 2,6-diisopropylphenol is subject to oxidative degradation. Oxygen free atmospheres include nitrogen, argon, or krypton gas, among others. Preferably, the compositions are manufactured, packaged, and stored under a nitrogen gas atmosphere.

6.3. Uses of Propofol Formulations

The present invention is also directed to methods of administering 2,6-diisopropylphenol to a subject in need of anesthesia, the methods comprising intravenously delivering to the subject a sterile pharmaceutical composition. Sterile pharmaceutical compositions acceptable for delivery to a subject are described herein. In one embodiment, a method is provided for administering 2,6-diisopropylphenol to a subject in need of anesthesia comprising intravenously delivering to the subject a sterile pharmaceutical composition comprising 2,6-diisopropylphenol, and one or more excipients; wherein the composition is substantially free of triacylglycerols. The composition also can be substantially free of other glyceryl esters of medium or long chain fatty acids or phospholipids as described herein.

The compositions of the present invention can be administered to a patient for the induction and/or maintenance of anesthesia, by administering an amount of the composition to a patient so that the patient receives an amount or dose of propofol that is effective for either inducing or maintaining anesthesia. The use of propofol as an anesthetic is known. Appropriate amounts and dosages of that drug for inducing and/or maintaining anesthesia are appreciated and can be readily determined by persons having ordinary skill in the relevant art(s). Generally, it is expected that between about 0.5 to 1.5 mg of propofol per kilogram of a patient's body weight should be administered over a time period of about 60 seconds to induce anesthesia in an adult, human patient. A dosage of between about 100 and 150 µg of propofol per kilogram of a patient's body weight is preferably administered to maintain anesthesia in the same patient.

The compositions can be parenterally administered to any animal, in particular, humans. In one embodiment, administration of a propofol containing composition comprises delivering the composition to a patient as a sole anesthetic, for example, via a bolus injection. In another aspect, administration of a propofol containing composition comprises delivering the composition to a patient for the induction of anesthesia and subsequently maintaining anesthesia with another anesthetic. Alternatively, administration of a propofol containing composition comprises delivering the composition to a patient for the induction and maintenance of longer-term anesthesia, for example, via continuous infusion. Further, the compositions can be delivered to a patient via intramuscular (i.e., IM) means, e.g., IM injection of propofol for induction and/or maintenance of anesthesia as well as other adjunct, desirable properties of compositions of the instant invention as described herein.

The propofol compositions comprise active agents in addition to propofol or, alternatively, the propofol compositions are co-administered with compositions comprising additional active agents. For example, the propofol containing compositions comprise or are co-administered with one or more local anesthetic agents to reduce or eliminate injection pain. If administered, local anesthetic agents preferably are administered in concentrations sufficient to reduce or eliminate injection pain. One of ordinary skill in the art can select and administer concentrations of local anesthetic agent(s) to achieve the desired effects without undue experimentation.

The propofol containing compositions can be administered to a patient using techniques commonly known in the art. For example, the compositions can be delivered intravenously to a patient via bolus injection or by infusion. Infusion of the propofol containing compositions can be made by directly infusing a composition or, alternatively, by addition of a propofol containing composition to an appropriate infusion solution such as 0.9% sodium chloride injection, 5% dextrose injection, or another compatible infusion solution.

In one embodiment, the compositions of the present invention are withdrawn, prior to administration, in multiple doses from a single container such as, for example, a vial or bag. For example, a composition of the invention is resistant to microbial growth even after multiple entries, e.g., with a syringe, into a single vial containing said composition. The multiple doses can be individually, or discretely, withdrawn such as by syringe or continuously withdrawn such as by continuous intravenous infusion. For example, doses of the present compositions are repeatedly withdrawn from a single vial over a course of treatment. Alternatively, a single dose may be withdrawn from a container over a course of treatment.

In one embodiment, the composition of the present invention allows use from a multi-use container. For example, a multi-use container would allow individual doses to be withdrawn from the same container at different timepoints or different days. Multi-use containers can be fashioned in a variety of structures or methods known in the art. Multi-use containers may be particularly useful for anesthesia of animals.

The quantity of propofol and method of delivery to a patient during administration can be varied, as determined appropriate, by the physician supervising the administration.

In addition to conventional uses of propofol, such as its use in anesthesia, the administration of compositions of the present invention are useful as an antioxidant by administering an effective amount of propofol to a patient in need thereof. If anesthesia is not desired, a sub-anesthetic dose may be administered in many cases. The propofol compositions of the present invention can be used for the prevention or reduction or treatment of oxidative injuries such as ischemia-reperfusion injuries. The propofol compositions can be used to inhibit oxidative damage induced by either hydrophilic or lipophilic radicals. The propofol compositions can be used to protect red blood cells and brain, liver, kidney, heart, lung and skeletal muscle organs, tissue and cells from oxidative stress and injury by pretreatment of an individual with an effective amount of propofol. The propofol compositions of the present invention are also useful to inhibit platelet aggregation by administering an amount of propofol effective to inhibit platelet aggregation. Both the enhancement of antioxidant capacity and antiplatelet effect of propofol, and particularly the propofol compositions of the present invention, make them particularly useful in coronary artery bypass surgery. In this indication propofol may be used, for example, at anesthetizing doses (for e.g., sufentanil 0.3 microg×kg(−1), propofol 1-2.5 mg×kg(−1) bolus then 100 microg×kg(−1) min(−1) before, and 50 microg×kg(−1)×min(−1) during CPB, or sufentanil 0.3 microg×kg(−1), propofol 2-2.5 mg×kg(−1) bolus then 200 microg×kg(−1)×min(−1).

Small-dose propofol sedation can also be used to attenuate the formation of reactive oxygen species, and thus oxidative stress and injury, in tourniquet-induced ischemia-reperfusion injury in patients under spinal anesthesia. An example of this use would be patients undergoing elective total knee replacement under intrathecal anesthesia.

Neuroprotection can further be provided by the propofol compositions, for e.g., by limiting the side-effect of vincristine in cancer therapy; reducing neural damage by attenuating lactate accumulation and oedema formation in focal or global cerebral ischaemia; and reducing oxygen-centered free radical brain injury associated with trauma and stroke.

The propofol compositions of this invention may also be used for sedation. For example, lower doses (e.g. compared to the dose necessary for anesthesia) of propofol can have a sedative effect on a patient. Patients are often sedated during emergency room procedures or prior to surgery to calm the patient.

Methods for administration and assaying the propofol compositions of the invention are routine in the art. Examples of methods of and assays can be found in: Runzer et al. Anesth Analg 2002 January 94(1):89-93; Eur J Anaesthesiol 2000 January 17(1):18-22; De La Cruz J P et al., Br J Pharmacol 1999 December; 128(7):1538-1544; Ansley D M et al., Can J Anaesth 1999 July 46(7):641-648; Murphy P G, et al., Br J Anaesth 1996 April 76(4):536-543; Daskalopoulos R et al. Glia 2002 August 39(2):124-132; Cheng Y J et al. Anesth Analg 2002 June 94(6):1617-1620; Wilson J X et al. J Neurosurg Anesthesiol 2002 January 14(1):66-79; Ergun R et al. Neurosurg Rev 2002 March 25(1-2):95-98; Li C R et al. Cell Biol Toxicol 2002 18(1):63-70.

In one aspect, the invention is directed to a composition of propofol which has a beneficial effect upon hemolysis of blood cells. The compositions of this invention may provide lower red blood cell lysis compared to emulsion propofol compositions, including but not limited to Diprivan. The compositions of this invention may also provide lower red blood cell lysis than saline solution. In a further aspect of this invention, the compositions of this invention may stabilize red blood cell membranes.

In one aspect, the instant invention is directed to a sterile aqueous pharmaceutical composition comprising 2,6-diisopropylphenol, and one or more excipients; wherein the propofol red blood cell-blood plasma partition coefficient ($K_p$) is about 3, is about 4, is about 5, is about 6, is about 7, is about 8, is greater than 3, is greater than 4, is greater than 5, is greater than 6, is greater than 7, is greater than 8, is greater than 9, or is greater than 10. Further, the instant invention is directed to a sterile aqueous pharmaceutical composition comprising 2,6-diisopropylphenol, and one or more excipients; wherein the propofol red blood cell-blood plasma partition coefficient ($K_p$) for the composition is at least about two times, is at least about 3 times, is at least about 4 times, or is at least about 5 times the $K_p$ obtained upon administration of a conventional propofol emulsion (e.g., Diprivan® or Propo-Flo™ or Rapinovet™) under the same delivery conditions. Additionally, the present invention includes a method of delivering propofol to a subject in need of anesthesia, the method comprising administering to a human or veterinary patient the sterile aqueous pharmaceutical composition described above. Preferably, the composition comprises two or more excipients, such as two or more surface active agents (e.g., two or more surfactants). Preferably, the composition is substantially free of triacylglycerols. The composition can be further substantially free of other glyceryl esters of medium or long chain fatty acids or phospholipids. In one embodiment, the propofol red blood cell-blood plasma partition coefficient, $K_p$, for the composition is at least about 3 times the $K_p$ obtained upon administration of a conventional propofol emulsion. In other embodiments, the propofol red blood cell-blood plasma partition coefficient, $K_p$, for the compositions of the instant invention is at least about 3, at least about 4, or at least about 5.

In another aspect, the instant invention is directed to a method of manipulating the blood plasma-red blood cell partition coefficient resulting from administration or delivery of a drug, for example a medicament or a therapeutic, diagnostic, or prophylactic agent such as propofol, to a patient. The blood plasma-red blood cell partition coefficient can be decreased or increased over the blood plasma-red blood cell partition coefficient resulting from administration or delivery of a conventional drug composition to a patient. Alternatively, compositions are prepared using the methods of the present invention that produce higher or lower blood plasma-red blood cell partition coefficients than compositions prepared using other methods. For example, particular formulations of the present invention are likely to increase the blood plasma-red blood cell partition coefficient resulting from administration or delivery of the instant propofol compositions over the blood plasma-red blood cell partition coefficient resulting from administration or delivery of Diprivan® Injectable Emulsion. The blood plasma-red blood cell partition coefficient is, for example, 2 or 3 times higher than the blood plasma-red blood cell partition coefficient resulting from administration or delivery of a conventional drug composition.

The method comprises preparing a pharmaceutical composition that comprises a drug and one or more excipients and wherein the pharmaceutical composition has a concentration of lipid excipients that is lower than the lipid concentration of an alternative composition comprising one or more lipids and wherein the alternative composition produces a lower blood plasma-red blood cell partition coefficient upon administration or delivery to a patient. In one embodiment, the drug is lipophilic (i.e., the drug has an affinity for, tends to combine with, or is capable of dissolving in lipids). In a preferred embodiment, the pharmaceutical composition comprises two or more excipients. Preferably, at least one excipient of the composition is a surface active agent such as, but not limited to, a surfactant. In a preferred embodiment, compositions are prepared that are substantially free of triacylglycerols. In one embodiment, the compositions are substantially free of other glyceryl esters of medium or long chain fatty acids or phospholipids as described herein. In one embodiment, the pharmaceutical composition is substantially free of lipid excipients.

The method comprises manipulating the concentration of lipid excipients to affect the partition of a drug between blood plasma and red blood cells. For example, the concentration of lipid excipients is reduced to increase the amount of drug that enters red blood cells thereby increasing the blood plasma-red blood cell partition coefficient.

Alternatively, the excipients and excipient concentrations of the instant invention can be manipulated to yield a composition that produces a blood plasma-red blood cell partition coefficient that is similar to that achieved by conventional drug formulations such as Diprivan® Injectable Emulsion. The excipients and excipient concentrations also can be manipulated to yield a composition that produces a blood plasma-red blood cell partition coefficient that is lower than that achieved by conventional drug formulations.

Methods for determining the blood plasma-red blood cell partition coefficient for a delivered drug are well known to those of ordinary skill in the art. Preferably, the propofol red blood cell-blood plasma partition coefficient for comparison purposes is obtained upon administration of a conventional propofol emulsion such as, for example, Diprivan® Injectable Emulsion. Diprivan® Injectable Emulsion is a widely available, commercially sold pharmaceutical product. The composition of Diprivan® Injectable Emulsion is also stated herein. Preferably, the conventional propofol emulsion and the composition of the instant invention are delivered under the same conditions. One of ordinary skill in the art can select appropriate experimental conditions and determine the propofol red blood cell-blood plasma partition coefficients ($K_p$) without undue experimentation.

Practice of the present invention provides several distinct advantages over conventional propofol compositions, in particular, emulsion formulations. In one aspect, the present invention relates to propofol containing compositions, and their administration to a patient in need of anesthesia, that do not contain triacylglycerols. In another aspect, the propofol containing compositions do not contain phospholipids. Such compositions eliminate the substrate for bacterial growth that those lipids can provide. In contrast, the oil-in-water emulsions of conventional propofol formulations contain lipids such as, for example, soybean oil and lecithin that are able to support the growth of microorganisms. Conventional propofol formulations, composed of lipids, glycerol, and large amounts of water in an isotonic environment with neutral to alkaline pH, provide a medium quite conducive to the growth of many microorganisms. As such, these oil-in-water emulsions require stringent handling, administration, and storage requirements. By reducing or substantially eliminating the presence of triacylglycerols and other microorganism supporting lipids and providing physical and chemical stability, the compositions of the present invention allow for more flexibility in handling, administration, and storage. Less restrictive handling and storage requirements allow for improved and expanded administration options, for example, in remote makeshift hospital settings. Further, the compositions of the present invention, with reduced or no lipid content, minimize, if not eliminate, the potential for contributing to or causing hyperlipidemia.

The aqueous propofol compositions of the invention provide some advantages over other aqueous formulations.

The aqueous propofol compositions of the invention minimize or even eliminate the requirements for antimicrobials, such as disodium edetate, or preservatives such as benzyl alcohol to retard the growth of microorganisms. In addition, these compositions allow for more flexibility and efficiency in administration and packaging. For example, the compositions of the present invention allow packaging to contain multiple doses in contrast to the single dose form of the current commercial propofol emulsions necessitated by sterility concerns. Advantageously, practice of the instant invention allows the withdrawal of multiple doses from a single vial over a period of time. Practice of the present invention also advantageously allows the use of tubing and opened portions of the propofol compositions for longer periods of time, e.g., longer than the currently recommended 12 hours, than are currently possible using conventional propofol compositions such as Diprivan® Injectable Emulsion.

7. EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing the invention in spirit or in scope. The invention is therefore to be limited only by the terms of the appended claims along with the full scope of equivalents to which those claims are entitled.

7.1. Preparation of Aqueous Propofol Samples

Exemplary propofol compositions can be prepared as follows and in accordance with the present invention. First, the excipients listed in Table I, below, are weighed out and pre-dissolved in de-ionized water at room temperature. The solution pH of each preparation is then adjusted using 2N sodium hydroxide to obtain a final pH of about 5.0. De-ionized water is added to bring the total volume of each preparation up to 100 milliliters. Lastly, 1000 mg of propofol and 200 mg of citric acid is added to each preparation, and the preparations are stirred using a magnetic stirrer at room temperature until the propofol was fully dispersed. Benzyl alcohol can also be included in the preparations, at an amount 0.45% (w/v).

Table 1, below, lists the contents of each exemplary preparation together with the final percent concentration in weight/volume (w/v) for each ingredient in 100 ml of water.

TABLE 1

EXEMPLARY PROPOFOL FORMULATIONS

| Formulation Identity: | Poloxamer 188 | PEG-400 | Propylene glycol | Propofol |
|---|---|---|---|---|
| M841 | 8% | 4% | 1% | 1% |
| M831 | 8% | 3% | 1% | 1% |
| M840 | 8% | 4% | 0% | 1% |
| M830 | 8% | 3% | 0% | 1% |
| M741 | 7% | 4% | 1% | 1% |
| M740 | 7% | 4% | 0% | 1% |
| M731 | 7% | 3% | 1% | 1% |
| M730 | 7% | 3% | 0% | 1% |
| M641 | 6% | 4% | 1% | 1% |
| M642 | 6% | 4% | 2% | 1% |
| M661 | 6% | 6% | 1% | 1% |
| M660 | 6% | 6% | 0% | 1% |
| M920 | 9% | 2% | 0% | 1% |

7.2. Physical Properties of Aqueous Propofol Preparations

The physical properties of aqueous propofol preparations, such as those described in the above example, can be evaluated as follows. First, the preparations' appearance (clear, hazy or less hazy) is evaluated with the naked eye to determine whether visible solids are present.

Particle sizes can also be estimated using Laser Light Scattering (LLS) particle size analysis, e.g., with a Zetasizer 300 HS available from Malvern Instruments, Inc. (Southborough, Mass.) according to the manufacturer's instructions. The polydispersity index can then be calculated for a formulation using the LLS data. Osmolality of a preparation can be determined, e.g., using a Vapor Pressure Osmometer (VAPRO), available from WESCOR, Inc. (Logan, Utah).

The physical stability of different preparations can be initially estimated by storing the preparations at room temperature and measuring one or more of the above-listed properties at periodic intervals (preferably at least once each day) to determine if an/or when the number or size of particles within the preparations changes.

Exemplary results for the formulations described in the previous example are set forth in Table 2, below.

TABLE 2

PHYSICAL PROPERTIES OF EXEMPLARY PROPOFOL FORMULATIONS

| Formulation Identity: | Avg. Particle Size (nm) | Polydispersity Index | Osmolality (mmol/kg) | Appearance | Physical Stability* (days) |
|---|---|---|---|---|---|
| M841 | 56 | 0.21 | 299 | Clear | 14 |
| M831 | 55 | 0.22 | 292 | Clear | 14 |
| M840 | 50 | 0.23 | 175 | Clear | 14 |
| M830 | 57 | 0.21 | 162 | Clear | 14 |
| M741 | 51 | 0.19 | 302 | Clear | 14 |
| M740 | 47 | 0.17 | 295 | Clear | 14 |
| M731 | 50 | 0.19 | 255 | — | — |
| M730 | 49 | 0.18 | 153 | — | — |
| M641 | — | — | — | Hazy | X† |
| M642 | 50 | 0.15 | 400 | Hazy | X† |
| M661 | 54 | 0.16 | 370 | Less Hazy | X† |
| M660 | — | — | — | Less Hazy | X† |
| M920 | 50 | 0.21 | — | Clear | 13 |

*Time during which no change in particle size is detected.
†"X" indicates that the sample is not a clear solution after fourteen days, and is not considered physically stable.

Data from a more detailed analysis of two preferred formulations (M841 and M831) are shown below, in Table 3. Briefly, preparations containing 2 mg/ml citric acid and 0.45% benzyl alcohol or, alternatively, 2 mg/ml and no benzyl alcohol are stored at 80° C. and at 4° C. The initial particle size and polydispersity index is measured as described above for each sample immediately before storage and at periodic intervals thereafter. The appearance of each preparation to the naked eye is also evaluated to determine whether it is clear or cloudy, indicating that propofol particles may have separated from the solution.

The different propofol formulations are stable for as long as four weeks across these various temperatures, and the presence or absence of benzyl alcohol does not adversely affect the physical stability of these preparations. The preparations remain as clear solutions at storage temperatures between about 25 and 80° C. However, at temperatures below about 25° C. the preparations become cloudy and the phase separates. The temperature at which this phase separation occurs is therefore referred to as the "cloud point," and can be determined by evaluating the physical appearance of preparations (clear or hazy) as they are slowly cooled. For example, the cloud point of the formulation M831 (with 2 mg/ml citric acid and 0.45% benzyl alcohol) is determined to be about 13° C., whereas the cloud point of M831 (2 mg/ml citric acid) without benzyl alcohol is very similar—about 16° C. The data shown in Table 3, below, show that even after storage at a temperature below the cloud point, formulations of the invention can be reconverted to a clear solution by allowing them to equilibrate at a temperature above the cloud point.

TABLE 3

PHYSICAL STABILITY OF PROPOFOL FORMULATIONS AT DIFFERENT STORAGE TEMPERATURES

| Formulation: | Initial Value | Stored at 80° C. | | Stored at 80° C. | |
| | | 2 weeks | 4 weeks | 2 weeks* | 2 weeks† |
|---|---|---|---|---|---|
| M841 (w/benzyl alkohol) | 47 nm (0.25) | 38 nm (0.18) | 38 nm (0.17) | 46 nm (0.19) | 42 nm (0.17) |
| M841 (w/o benzyl alcohol) | 55 nm (0.21) | | | 46 nm (0.19) | 42 nm (0.17) |
| M831 (w/benzyl alcohol) | 47 nm (0.25) | 36 nm (0.17) | 37 nm (0.17) | 48 nm (0.22) | 41 nm (0.17) |
| M831 (w/o benzyl alcohol) | 55 nm (0.21) | 42 nm (0.16) | 42 nm (0.16) | 97 nm (0.70) | 54 nm (0.16) |

*Measured after equilibrating at room temperature for three hours.
†Measured after equilibrating at room temperature for two days.

7.3. Chemical Stability of Aqueous Propofol Preparations

The chemical stability of aqueous propofol preparations, such as those described in the above examples, can be evaluated using routine techniques. For example, propofol containing compositions can be subjected to a variety of environmental conditions, after which the stability of propofol and/or the excipients is evaluated using high performance liquid chromatography (HPLC). Briefly, the sample can be diluted in an aqueous mixture containing 60% acetonitrile, and injected onto a C18 column operated at 45° C. A two component gradient mobile phase is run consisting of: (a) 0.05% TFA in water, and (b) 0.05% in acetonitrile. The run time is preferably about 55 minutes with a flow rate of 0.8 ml/min. Propofol will typically elute from the C18 column after about 21 minutes. Eluting propofol can be detected, along with various impurities and degradation products, by monitoring the elute's UV absorption at 272 nm. The amounts of different impurities can be estimated by measuring the area under their peak's on the HPLC chromatogram, and normalizing that area to the area under the peak corresponding to propofol.

FIGS. 1-4 each show the exemplary results of such an analysis for various propofol preparations stored over time (indicated in weeks) under different environmental conditions. In each instance, the amount of propofol remaining in each preparation (indicated as percentage of the initial propofol content) can be estimated from the peak area of propofol, which elutes from the C18 column about 21 minutes into the gradient run.

Figure 1:
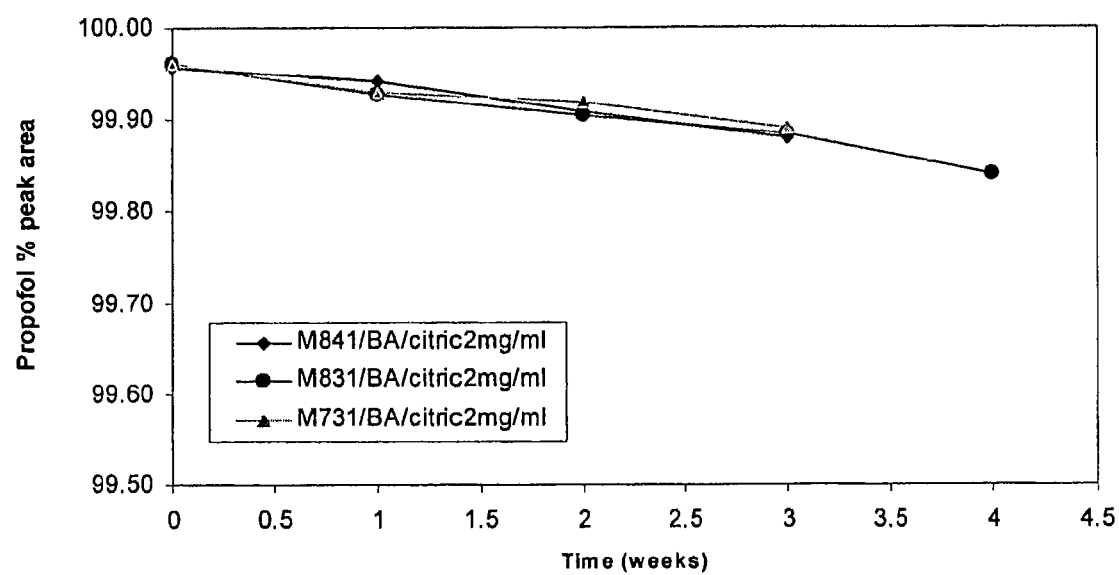

In more detail, FIG. 1 shows exemplary results for various propofol formulations from Table I, supra, that are stored at 80° C., to simulate non-ideal or "stressed" storage conditions to which a propofol formulation may be subjected. These data indicate that all of the compositions are highly stable under such conditions, with less than 0.2% propofol degradation even after four weeks of storage under these conditions. Because formulations with minimal levels of excipients are generally preferred, the formulation M831 was selected for further analysis.

Figure 2A:
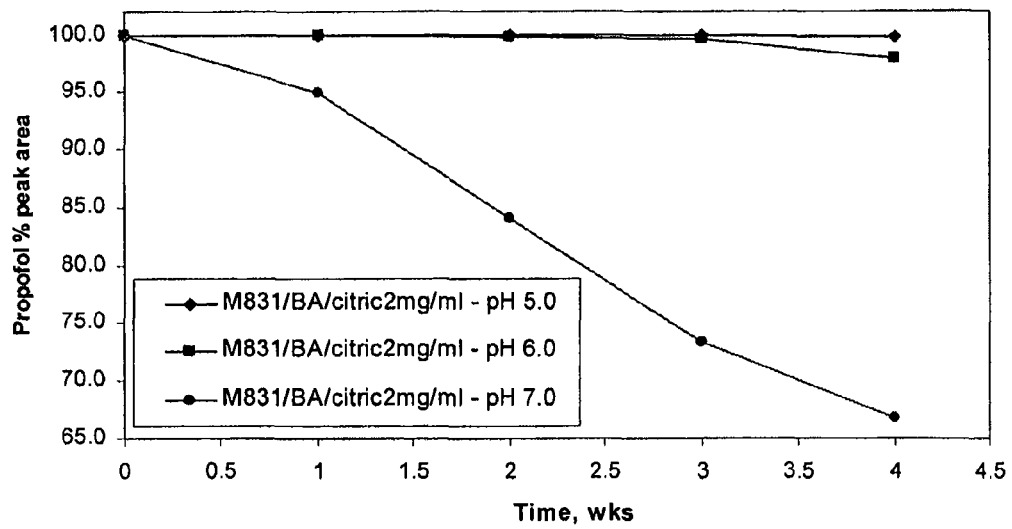
Figure 2B:
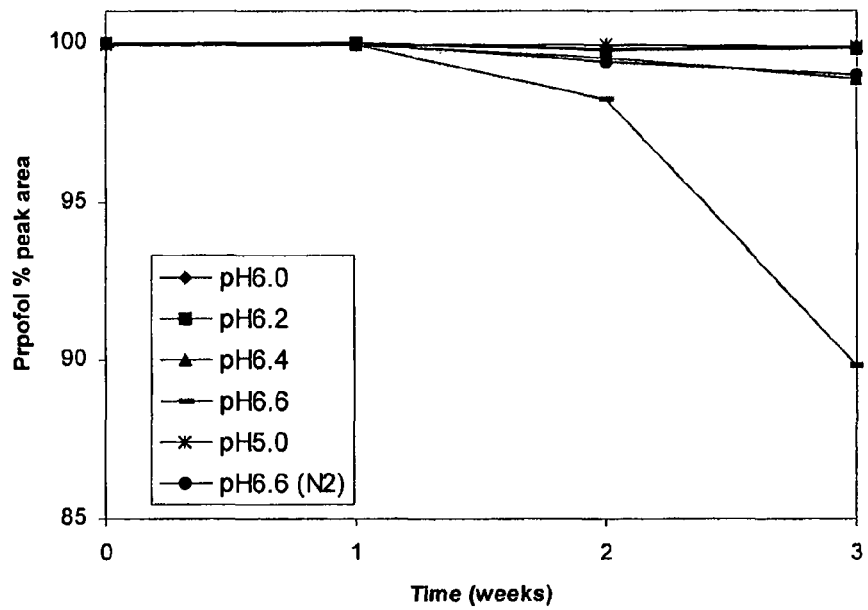
Figure 3:
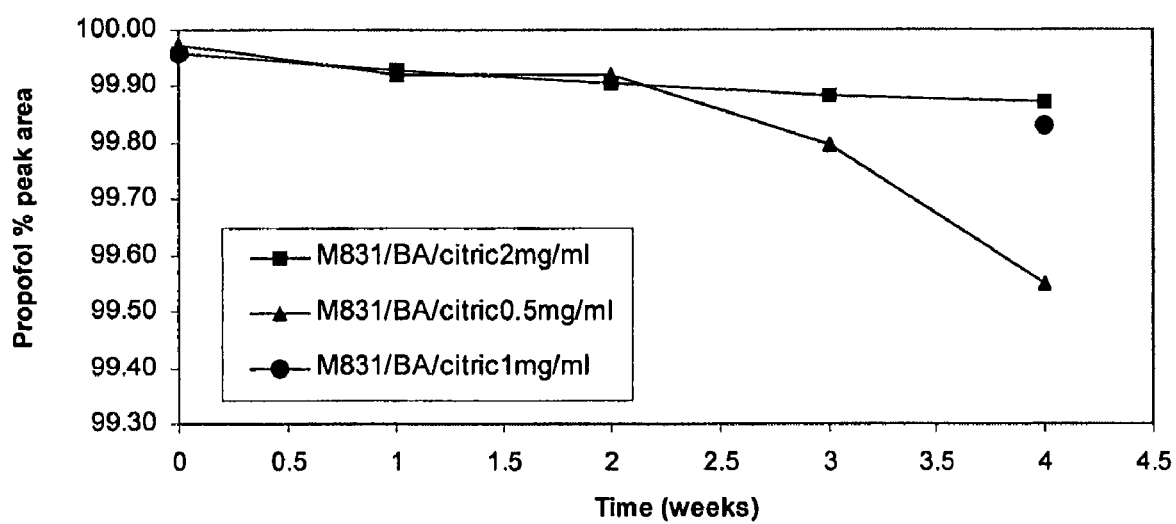

FIGS. 2A-2B show exemplary data from the analysis of the M831 formulation stored at 80° C. at a under a variety of different pH conditions, demonstrating that the formulation is remarkably stable at pH levels as high as about 6.2. FIG. 3 shows exemplary data from the analysis of M831 formulations (stored at pH 5 and 80° C.) containing different levels of citric acid. These data demonstrate that the presence of citric acid in aqueous propofol formulations of the invention (preferably at concentrations of about 2 mg/ml) greatly improves the stability.

Figure 4:
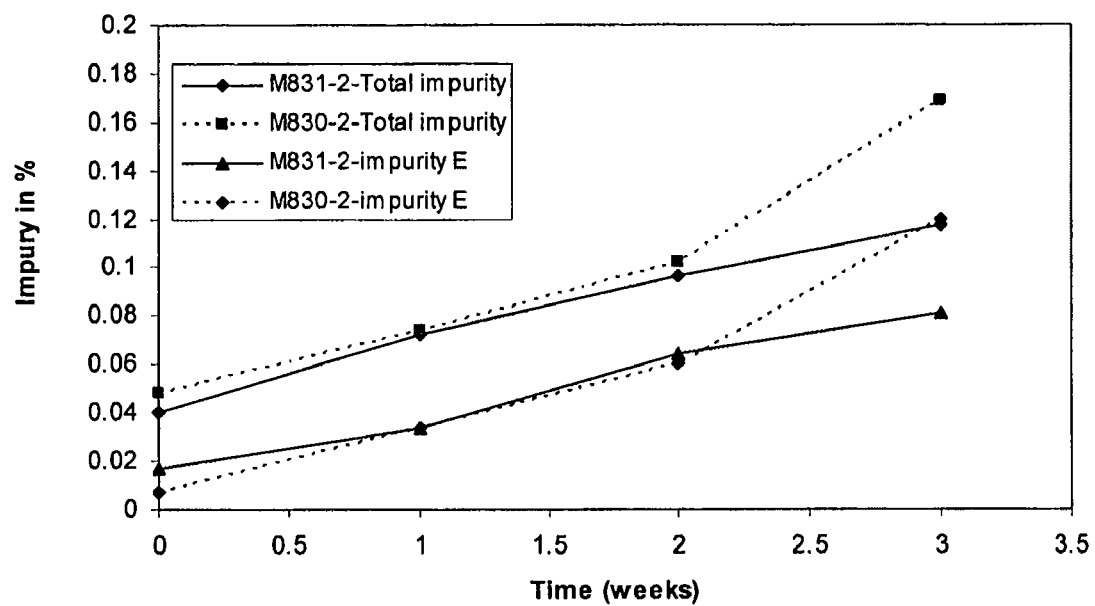

FIG. 4 shows exemplary data from the HPLC analysis formulations M831 and M830, which contain 1% and 0% propylene glycol (w/v), respectively. Both samples additionally contain benzyl alcohol (0.45% w/v) and citric acid (2 mg/ml) In these data, the purity of each preparation is estimated by measuring the area under curves associated with degradation production of propofol. These data show that the amount degradation products increases rapidly in formulations containing no propylene glycol, whereas the level of degradation products remain relatively stable in degradation products that contain a small amount (e.g., about 1%) or propylene glycol.

7.4. Commercial Manufacture of Aqueous Propofol Formulations

Aqueous propofol formulations of the present invention can be readily manufactured in a manner substantially similar to the preparation of laboratory samples described in the preceding examples. As an example and without being limited to any particular method or embodiment, purified water for injection (WFI) and block polymer (e.g., poloxamer 188) can be combined in a formulation vessel and stirred until the block polymer is dissolved. Other excipients (preferably a polyethylene glycol such as PEG-400, a propylene glycol, citric acid and benzyl alcohol) are then added and mixed until all of these ingredients are dissolved. The pH is then adjusted to 5.5±0.5 using sodium hydroxide solution. Propofol is then added and the solution is mixed until propofol is fully dissolved.

Water for injection is then added to achieve a target batch weight. The final formulation is then sterilized by filtration through a 0.2 μm nominal pore sized filtered. The filtered solution can be aseptically filled into glass vials, stoppered and capped. Preferably, the finished vials are inspected for particles or other defects before packaging.

In the above described method, block polymer is preferably added first, followed in order by pH titration and the addition of propofol. The order in which other ingredients are added to the composition is not significant.

7.5. Further Aqueous Propofol Examples

Example 1

A propofol containing composition (Formulation C) was prepared as follows. Approximately 500 mg PEG-400, 350 mg PEG-40 stearate, and 35 mg polyoxyethylene 20 sorbitan monooleate were added to a glass vessel. Purified water was added followed by 100 mg propofol. Water was added as necessary to bring the total volume to 10 milliliters. The mixture was stirred at room temperature using a magnetic stirring bar for at least 4 hours over a 24-hour period. The resulting composition was substantially transparent to the naked eye but slightly hazy.

Laser Light Scattering (LLS) particle size analysis was performed using a Zetasizer 3000HS (Malvern Instruments Inc., Southborough, Mass.). Particle size was determined to be less than approximately 100 nanometers.

Example 2

A propofol containing composition (Formulation D) was prepared as follows. Approximately 300 mg Poloxamer 237 and 600 mg PEG-400 were added to a glass vessel. Purified water was added followed by 100 mg propofol. Water was added as necessary to bring the total volume to 10 milliliters. The mixture was stirred at room temperature using a magnetic stirring bar for at least 4 hours over a 24-hour period. The resulting composition was clear to the naked eye with no visible solids present.

Example 3

A propofol containing composition (Formulation F) was prepared as follows. 3.0 g polyoxyethylene 20 sorbitan monooleate, 2.9 g propylene glycol, 8.0 g PEG-400, 10.0 g Poloxamer 188, and 0.4 g citric acid were added to a 250 mL volumetric flask. Deionized water was added to the 150 mL marker and the contents of the flask were stirred for 3 hours. Additional deionized water was added to bring the total volume to 197.8 mL and the solution was stirred for one hour. 2.2 mL of 100% pure propofol was added to the flask and the contents of the flask were stirred for at least 8 hours (i.e., until all of the propofol droplets had dissolved). The mixture was filtered through a PVDF filter with a 0.2 micron pore size. The resulting composition was clear to the naked eye. HPLC analysis indicated that less than 1% of propofol was retained by filtration. Since the HPLC assay had a 1-2% variation, this less than 1% loss is not considered significant. Laser Light Scattering (LLS) particle size analysis was performed using a Zetasizer 3000HS (Malvern Instruments Inc., Southborough, Mass.) Particle size was determined to be approximately 20 to 100 nanometers. Physical stability of Formulation F was monitored by measuring mean particle size over the course of a 4 week study. Mean particle size was initially measured as 89±6 nanometers. A sample of Formulation F was held at 60° C. for 4 weeks. At the end of the time period, mean particle size of Formulation F was 84±6 nanometers.

Example 4

Propofol containing Formulations C, D and F were prepared as in Examples 1, 2 and 3, respectively. The compositions were separately sealed in glass vials. The compositions then were subjected to a variety of environmental conditions. Reverse phase HPLC was used as an indicator of propofol and excipient chemical stability. HPLC conditions are shown in Table 4 below.

TABLE 4

| HPLC Conditions | |
|---|---|
| Column | Chromolith Performance RP-18e (Merck Kga) 4.6 × 100 mm |
| Mobile Phase | 45% 50 mM $KPO_4$; pH 2.5; acetonitrile |
| Flow Rate | 4.5 mL/min |
| Temperature | 35° C. |
| Column | Ambient |
| Sample | |
| Injection Volume | 15 microliters |
| Run Time | 5 minutes |
| Detection | UV, 272 nm |

Prior to HPLC analysis, compositions were held at the indicated conditions for 4 weeks. HPLC was also performed on initially formed compositions. The percent of propofol degradation increase after 4 weeks is summarized in Table 5 below.

TABLE 5

| Increase in the Percent of Total Propofol Degradates after 4 weeks. | | |
|---|---|---|
| Formulation | 25° C. | 40° C. |
| C | 0.50 | 3.7 |
| D | 0.1 | 0.64 |
| F | None detected | 0.07 |

Analysis of degradates is the most sensitive way to gauge stability of relatively stable materials, such as the present propofol compositions, over a short period of time. The temperature increase from 25 to 40° C., the latter temperature representing accelerated conditions, was responsible for increasing amounts of oxidation in each case. The two degradation products detected are likely a quinone and a dimer. Based on this data, propofol contained in Formulations D and F is predicted to possess stability at room temperature for periods of time greater than 4 weeks. High temperature stability (i.e., at 40° C.) of Formulation F indicates a projected propofol stability of about 1 to 2 years under refrigerated conditions.

Example 5

Propofol containing Formulation F was prepared as in Example 3. Samples of the compositions were separately sealed in glass vials and then were held at the temperatures indicated in Table 5 for the indicated amount of time. HPLC analysis of the samples was performed using the methods of Example 4. Table 6 shows the total degradates as percent of peak area by HPLC measured in Formulation F as a function of time and temperature.

TABLE 6

Total degradates (percent of peak area by HPLC) in Formulation F as a function of time and temperature

| Time | Temperature | | |
|---|---|---|---|
| | 25° C. | 40° C. | 60° C. |
| 4 weeks | None detected | None detected | None detected |
| 8 weeks | <0.1 | <0.1 | <0.1 |
| 12 weeks | 0.44 | 1.01 | 1.30 |

The data presented in Table 6 demonstrates that compositions of Formulation F are stable for at least three months.

Example 6

Propofol Formulations C and D were made having the same compositions, and prepared by the same methods, as Examples 1 (Formulation C) and 2 (Formulation D). These compositions, along with Diprivan® Injectable Emulsion (AstraZeneca) as a control, were then evaluated in vivo for pharmacokinetic profiles.

Adult male Sprague-Dawley rats were obtained from Charles River Canada, Inc. (St. Constant, Quebec, Canada). At the time of use, the animals each weighed about 250 to 290 grams. The overall design for the animal study is summarized in Table 7.

TABLE 7

In vivo Pharmacokinetic Study Design

| Group | Formulation | Dose (mg/kg) | Dose Volume (mL/kg) | Number of Animals | Samples Collected |
|---|---|---|---|---|---|
| 1 | Control | 10 | 1 | 4 | Plasma |
| 2 | | | | 4 | Blood |
| 3 | C | 10 | 1 | 4 | Plasma |
| 4 | | | | 4 | Blood |
| 5 | D | 10 | 1 | 4 | Plasma |
| 6 | | | | 4 | Blood |

Formulations were administered to the animals by intravenous injection via a jugular vein. The formulations were administered at a dose volume of 1 mL/kg over a period of approximately 1 minute (slow push) via jugular venipuncture under isoflurane anesthesia. As shown in Table 7, each formulation was administered to 2 groups of 4 animals. Animals were randomly selected to fill the study groups on the basis of comparable body weights.

Following administration, blood samples (0.25 to 0.40 mL) were collected by jugular venipuncture under anesthesia from each of the animals at pre-dose (i.e., immediately following completion of dose administration), 2, 3, 5, 7, 10, and 15 minutes from the start of dose administration. The animals were maintained in dorsal recumbancy during both dose administration and during blood sampling.

Blood samples from groups 2, 4, and 6 were stored at −20° C. nominal pending further analysis. Blood samples from groups 1, 3, and 5 were centrifuged at 3200 g at 4° C. nominal for 10 minutes. The resulting plasma samples were harvested and stored at −20° C. nominal pending further analysis.

The animals were observed constantly during dose administration and blood sampling. The time for the animals to regain ventral recumbancy was recorded as an indication of duration of anesthesia. Table 8 shows the mean time to first animal movement and the mean time to regain ventral recumbancy, along with standard deviations, for each of the formulations evaluated.

TABLE 8

Observations on the Effects of Anesthesia

| Group | Formulation | Mean Time to First Movement (min) (S.D.) | Mean Time to Regain Ventral Recumbancy (min) (S.D.) |
|---|---|---|---|
| 1 and 2 | Control | 11.6 (3.9) | 17.5 (4.1) |
| 3 and 4 | C | 13.5 (4.7) | 15.6 (2.2) |
| 5 and 6 | D | 10.8 (4.1) | 14.4 (2.8) |

All plasma and blood samples were analyzed for propofol concentration using LC-MS/MS. Pharmokinetic analysis of propofol in plasma and blood were performed using the PhAST software program (Version 2.3, Phoenix International Life Sciences, Inc, Saint-Laurent, Quebec, Canada).

The area under the concentration-time curve between 0 and 15 minutes ($AUC_{0-15}$) was lower in plasma following administration of the novel propofol compositions (i.e., Formulations C and D) relative to the emulsion control. Propofol clearance (CL) was relatively similar following administration of Formulations C and D and the control. A significant increase in the volume of distribution (Vss) was observed for Formulations C and D from the plasma data (Table 9) and reflects distribution of the drug from plasma into other tissues. An inverse correlation existed between the volume of distribution in plasma and the particle size of the formulations; the emulsion control had micrometer-size droplets while the novel propofol compositions' particles were below 100 nanometers in size. The blood data, obtained by assaying whole blood at each time point for the presence of drug, showed comparable parameters between formulations (Table 10) indicating mass balance of the drug at an equivalent dose. The combined data of Tables 9 and 10 strongly suggest that the nature of the formulation, in particular particle size and availability of propofol to the aqueous medium, plays an important role in determining plasma-blood partitioning of this highly lipophilic drug.

TABLE 9

Mean, ± Standard Deviation, pharmacokinetic parameters of propofol in plasma following a single intravenous dose (10 mg/kg) of a novel propofol formulation (C or D) and a commercially available emulsion formulation in male Sprague-Dawley rats.

| Parameter | Formulation C | Formulation D | Control Emulsion Formulations |
|---|---|---|---|
| $AUC_{0-15}$ (mcg.min/mL) | 14.4 ± 3.2† | 18.4 ± 2.2 | 31.1 ± 8.9 |
| CL (mL/min/kg) | 456 ± 113† | 254 ± 80 | 242 ± 31 |
| Vss (mL/kg) | 5342 ± 1145† | 7338 ± 2748 | 2595 ± 612 |

†$p < 0.05$ vs Control Emulsion Formulation.

TABLE 10

Mean, ± Standard Deviation, pharmacokinetic parameters of propofol in blood following a single intravenous dose (10 mg/kg) of a novel propofol formulation and a commercially available emulsion formulation in male Sprague-Dawley rats.

| Parameter | Formulation C | Formulation D | Control Emulsion Formulations |
|---|---|---|---|
| $AUC_{0-15}$ (mcg.min/mL) | 62.7 ± 16† | 60.2 ± 11 | 45.5 ± 6.2 |
| CL (mL/min/kg) | 112 ± 20† | 88 ± 27 | 192 ± 30 |
| Vss (mL/kg) | 1516 ± 596 | 1820 ± 550 | 1292 ± 183 |

†$p < 0.05$ vs Control Emulsion Formulation.

Using historical values of red blood cell (RBC) counts in rats, calculations were performed to obtain the area under the concentration-time curve ($AUC_{0-15}$) and the plasma-RBC partition coefficient ($K_p$) for Formulations C and D, as examples of novel propofol compositions, and compared to calculations made for Diprivan® Injectable Emulsion. The fraction of propofol sequestered in RBC with Formulations C and D appear to be markedly higher than that of the emulsion formulation (Table 11).

Following intravenous administration, it appears that propofol from the novel composition concentrates in lipid-rich areas of blood, which participate in the uptake and transfer to its active site and provide anti-platelet and antioxidant activity during anesthesia. Since propofol affinity for whole blood and RBC is an important determinant on the onset, intensity and duration of anesthesia, the results support the hypothesis that the novel composition of propofol can enhance or even optimize the in vivo pharmacological activity of the drug. These results also indicate that additional benefits such as improved resistance of erythrocytes to physical and hemodynamic stress during anesthesia, a greater preservation of red blood cell counts after surgery, and a reduction of reperfusion injury in surgery may be associated with the use of the novel propofol compositions of the present invention.

TABLE 11

Calculated Mean ± Standard Deviation $AUC_{0-15}$ and $K_p$ of propofol in RBC following a single intravenous dose (10 mg/kg) of a novel propofol composition (Formulations C and D) and a commercially available emulsion formulation in male Sprague-Dawley rats.

| Parameters | Formulation C | Formulation D | Diprivan ® Injectable Emulsion |
|---|---|---|---|
| $AUC_{0-15}$ (mcg.min/mL) | 59.0 ± 20.6† | 59.7 ± 22.3† | 17.6 ± 3.0 |
| $K_p$ (RBC:Plasma) | 8.74 ± 3.09† | 6.31 ± 0.89† | 2.03 ± 0.16 |

†$p < 0.05$ vs Diprivan ® Injectable Emulsion.

Example 7

In vitro hemolysis of TPI-213F (1% w/w propofol, 5% w/w poloxamer 188, 4% w/w PEG 400, 1.5% w/w polysorbate 80, 1% w/w propylene glycol, and 2 mg/ml citric acid) was assessed using fresh human whole blood. This study was performed at MDS Pharma Services (Montreal, Canada). Blood was obtained from 2 human volunteers of mixed gender and compatible blood type. Blood samples were pooled and spiked with stock solutions of Diprivan® or TPI-213F in plasma to final concentrations of 10 ug/mL. A saline control was tested to establish auto-lysis of the red blood cells. All samples were incubated at 37° C. At 15, 45 min and 1, 1.5, and 2 hours post-onset of incubation, aliquots (in triplicate) of the whole blood were removed from each sample and centrifuged at 3,200 g for 10 min to obtain plasma. The plasma samples were analyzed for hemoglobin content by measuring the absorbance at 415 nm Visual appraisal of hemolysis prior to hemoglobin content determination indicated that there was evidence of hemolysis in all Diprivan® samples at 2 hour following onset of incubation. In contrast, no visual evidence of hemolysis was observed for any TPI-213F samples at any of the time points.

Mean concentrations of hemoglobin in plasma following incubation with increasing amount of Diprivan® and TPI-213F were measured. Consistent with visual appraisal observations, TPI-213F showed lower hemoglobin ($p<0.05$, the student's t test) concentrations at all time points compared to Diprivan®. This indicates that TPI-213F is milder on red blood cells than Diprivan®.

The hemoglobin concentration in plasma following incubation with the saline control establishes the baseline from auto-lysis of the red blood cell over time. Compared to this baseline, the TPI-213F related samples showed lower hemolysis ($p<0.025$, the student's t test), indicating that the components in TPI-213F have a stabilizing effect on the red blood cell membrane. In contrast, all Diprivan® samples showed more hemolysis than saline at later time points (after 1 hr incubation, $p<0.05$).

Example 8

A pharmacokinetic study was carried out at MDS Pharma Services in beagle dogs (weight 8-10 kg) to compare TPI-213M (1% propofol w/v, 8% poloxamer 188 w/v, 3% PEG-400 w/v, 1% propylene glycol w/v, 20 mg/ml citric acid, 0.45% benzyl alcohol w/v) and RAPINOVET (a currently marketed lipid based emulsion). All animals were handled according to established guidelines and principles. Administration of all formulations was achieved via slow push over a period of about 1 min through an indwell catheter. All dogs received the same dosing regiment in a cross-over design as follows:

TABLE 12

| Dosing Day | Formulation | Dose (mg/kg) | Dose Volume (mL/kg) | No. of Dogs | Sample collected |
|---|---|---|---|---|---|
| Day 1 | TPI-213M | 6 | 0.6 | 3 | Plasma, blood |
| Day 1 | Rapinovet | 6 | 0.6 | 3 | Plasma, blood |
| Day 8 | Rapinovet | 6 | 0.6 | 3 | Plasma, blood |
| Day 8 | TPI-213M | 6 | 0.6 | 3 | Plasma, blood |

Following dose administration, blood samples were collected at various time points. An aliquot of blood was removed for analysis and the remaining blood was centrifuged at 3,200 g at 4° C. for 10 min. The resulting plasma samples were harvested and stored at −20° C. for analysis of propofol.

The pharmacokinetic parameters calculated for TPI-213M and Rapinovet are shown in Table 13. TPI-213M showed similar plasma concentrations compared to Rapinovet, suggesting that TPI-213M is bioequivalent to Rapinovet. Both formulations also showed similar propofol concentrations and AUC values in blood as in plasma, suggesting that there is no preferential partitioning of the drug into dog red blood cells from either formulation. This is different from what was seen in the rats, pointing to species-related differences in red blood cell partitioning.

TABLE 13

Mean pharmacokinetic parameters for propofol in plasma and blood following a single intravenous dose of Rapinovet or TPI-213M to Beagle Dogs. Values shown are mean ± standard deviation.

| Test Group | Article | Matrix | Dose (mg/kg) | $AUC_{(0-\infty)}$ (ng · hr/mL) | $t_{1/2}$ (hr) | $V_{dss}$ (mL/kg) | CL (mL/hr · kg) |
|---|---|---|---|---|---|---|---|
| 1 | TPI-213M | Plasma | 6 | 929 ± 128 | 0.38 ± 0.15 | 3056 ± 539 | 6553 ± 834 |
| 2 | TPI-213M | Blood | 6 | 746 ± 249 | 0.36 ± 0.07 | 4594 ± 3511 | 9121 ± 4200 |
| 3 | Rapinovet | Plasma | 6 | 1052 ± 255 | 0.41 ± 0.30 | 2509 ± 1476 | 6051 ± 1747 |
| 4 | Rapinovet | Blood | 6 | 892 ± 320 | 0.29 ± 0.03 | 2485 ± 1297 | 7869 ± 4111 |

$AUC_{0-\infty}$: The area under the concentration vs. time curve from time zero to infinity
$t_{1/2}$: Terminal phase half-life
$V_{dss}$: Apparent volume of distribution
CL: Plasma or blood clearance During this pharmacokinetic study, the dogs were also observed for the pharmacological effect from the two formulations, i.e., time to sleep and time to full awakeness. The data suggests that TPI-213M has the same pharmacological effect as Rapinovet.

8. REFERENCES CITED

Various references, including patents, patent applications and various publications, are cited and discussed in the description of this invention. The citation and/or discussion of any such reference is provided merely to clarify the description of the present invention and is not an admission that any such reference is "prior art" to the invention described here. All references cited and/or discussed in this specification are incorporated herein by reference in their entirety and to the same extent as if each reference was individually incorporated by reference.

What is claimed is:

1. An aqueous formulation consisting essentially of, on a gram per 100 ml (reported as %) basis: 1-2% 2,6-diisopropylphenol; water; and up to 15% excipients, wherein the excipients consist essentially of 2% to 6% polyethylene glycol (PEG), 5% to 9% poloxamer 188, at least one preservative, and optionally, one or more antimicrobial agents, pH modifiers, stabilizers, or tonicity modifiers, and wherein the formulation is an aqueous solution including less than 1% lipids and being clear to the naked eye.

2. The formulation of claim 1, wherein the at least one preservative comprises citric acid or a salt thereof.

3. The formulation of claim 2, wherein the citric acid or salt thereof is present in an amount between about 0.05% and 3%.

4. The formulation of claim 2, wherein the citric acid or salt thereof is present in an amount between about 0.05% and about 0.2%.

5. The formulation of claim 2, wherein poloxamer 188 is present in an amount of about 8% of the formulation, PEG is present in an amount of about 3% of the formulation, propylene glycol is present in an amount of about 1% of the formulation, the citric acid or salt thereof is present in an amount of about 0.2% of the formulation, and 2,6-diisopropylphenol is present in an amount of about 1% of the formulation.

6. The formulation of claim 5, wherein the PEG is PEG-400.

7. The formulation of claim 1, wherein the excipients include an antimicrobial agent selected from the group consisting of disodium edetate, metabisulfate, benzyl alcohol, cysteine or a salt thereof, and EDTA.

8. The formulation of claim 7, wherein the antimicrobial agent is benzyl alcohol in an amount of up to 0.5% of the formulation.

9. The formulation of claim 1, wherein the excipients include propylene glycol in an amount not more than 5% of the formulation.

10. The formulation of claim 9, wherein the amount of propylene glycol is not more than 2% of the formulation.

11. The formulation of claim 10, wherein the amount of propylene glycol is 1% to 2% of the formulation.

12. The formulation of claim 1, wherein the excipients include polysorbate.

13. An aqueous formulation consisting essentially of, on a gram per 100 ml (reported as %) basis: 1-2% 2,6-diisopropylphenol; water; and up to 15% excipients, wherein the excipients consist essentially of about 4% polyethylene glycol (PEG), about 1% propylene glycol, about 5% poloxamer 188, about 1.5% polysorbate 80, and optionally, one or more pH modifiers, stabilizers, or tonicity modifiers, and wherein the formulation is an aqueous solution including less than 1% lipids and being clear to the naked eye.

14. The formulation of claim 13, wherein the excipients include citric acid or a salt thereof.

15. The formulation of claim 14, wherein the citric acid or salt thereof is present in an amount of about 0.2% of the formulation.

16. The formulation of claim 14, wherein the PEG is PEG-400.

17. An aqueous formulation consisting essentially of, on a gram per 100 ml (reported as %) basis: about 1% 2,6-diisopropylphenol, water, and up to 15% excipients, wherein the excipients consist essentially of about 6% polyethylene glycol (PEG), about 6% poloxamer 188, and optionally, one or more pH modifiers, stabilizers, or tonicity modifiers, wherein the formulation is an aqueous solution including less than 1% lipids and being clear to the naked eye.

18. The formulation, of claim 17, wherein the PEG is PEG-400.

19. An aqueous formulation consisting essentially of, on a gram per 100 ml (reported as %) basis: about 1% 2,6-diisopropylphenol; water; and up to 15% excipients, wherein the excipients consist essentially of about 6% polyethylene glycol (PEG), about 3% poloxamer 237, and optionally, one or more pH modifiers, stabilizers, or tonicity modifiers, wherein the formulation is an aqueous solution including less than 1% lipids and being clear to the naked eye.

20. The formulation of claim 19, wherein the PEG is PEG-400.

21. An aqueous formulation consisting essentially of, on a gram per 100 ml (reported as %) basis: about 1-2% 2,6-diisopropylphenol; water; and up to 15% excipients, wherein the excipients consist essentially of about 2% to about 6% polyethylene glycol (PEG), about 5% to about 9% poloxamer 188, at least one preservative, and optionally, one or more antimicrobial agents, pH modifiers, stabilizers, or tonicity modifiers, and wherein the formulation is an aqueous solution including less than 1% lipids and being clear to the naked eye.

22. The formulation of claim 21, wherein said excipients include propylene glycol at a concentration of not more than 5% of the formulation.

23. The formulation of claim 21, wherein said at least one preservative comprise citric acid or a salt thereof.

24. The formulation of claim 23, wherein the citric acid or salt thereof is present in an amount between about 0.05% and about 0.2%.

25. The formulation of claim 21, wherein the excipients include an antimicrobial agent selected from the group consisting of disodium edetate, metabisulfate, benzyl alcohol, cysteine or a salt thereof, and EDTA.

26. The formulation of claim 25, wherein the antimicrobial agent is benzyl alcohol in an amount of up to 0.5% of the formulation.

27. The formulation of claim 21, wherein the excipients include polysorbate.

28. The formulation of claim 21, wherein the PEG is PEG-400.

29. A formulation comprising an injectable anesthetic solution, including at least one preservative as an optional component, the formulation including no more than 15% (weight/volume grams/100 ml) excipients and consisting essentially of, in addition to said optional components, a clear aqueous composition selected from the group consisting of:
(a) 1% 2,6-diisopropylphenol, 7% poloxamer 188, 3% PEG-400, and water;
(b) 1% 2,6-diisopropylphenol, 7% poloxamer 188, 3% PEG-400, 1% propylene glycol, and water;
(c) 1% 2,6-diisopropylphenol, 6% poloxamer 188, 6% PEG-400, and water;
(d) 1% 2,6-diisopropylphenol, 6% poloxamer 188, 6% PEG-400, 1% propylene glycol, and water;
(e) 1% 2,6-diisopropylphenol, 6% poloxamer 188, 4% PEG-400, 1% propylene glycol, and water;
(f) 1% 2,6-diisopropylphenol, 6% poloxamer 188, 4% PEG-400, 2% propylene glycol, and water; and,
(g) 1% 2,6-diisopropylphenol, 5% poloxamer 188, 4% PEG-400, 1% propylene glycol, and water, wherein said formulation includes less than 1% lipids.

* * * * *